United States Patent
DiFoggio

(12) 
(10) Patent No.: US 6,420,869 B1
(45) Date of Patent: Jul. 16, 2002

(54) METHOD AND APPARATUS FOR ESTIMATING NMR PROPERTIES BY NEAR INFRARED SPECTRA

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/690,642

(22) Filed: Oct. 17, 2000

(51) Int. Cl.[7] .................................................. G01V 3/00
(52) U.S. Cl. ........................................ 324/303; 324/300
(58) Field of Search ................................ 324/303, 300, 324/322, 309

(56) References Cited

U.S. PATENT DOCUMENTS

| | | | |
|---|---|---|---|
| 5,055,787 A | 10/1991 | Kleinberg et al. | 324/303 |
| 5,668,374 A | 9/1997 | DiFoggio et al. | 250/339.12 |
| 5,939,717 A | 8/1999 | Mullins | 250/255 |

FOREIGN PATENT DOCUMENTS

GB  2217838  11/1989

OTHER PUBLICATIONS

Article titled: "Guidelines for Applying Chemometrics to Spectra: Feasibility and Error Propagation"; Author: Rocco DiFoggio; Publication: Applied Spectroscopy; vol. 54, No. 3, Mar. 2000, pp.94A–113A.

*Primary Examiner*—Edward Lefkowitz
*Assistant Examiner*—Brij B. Shrivastav
(74) *Attorney, Agent, or Firm*—Madan, Mossman & Sriram, P.C.

(57) ABSTRACT

By developing correlations between near-infrared spectra (NIR) and the T1 and T2 Nuclear Magnetic Resonance (NMR) decay times of known crude oils, we can then use near-infrared measurements to predict T1 and T2 decay times of unknown crude oils. The purpose is to use NIR to predict NMR parameters of crude oils while they are being sampled downhole by a formation tester and to use these predictions to improve log interpretation of NMR logs.

8 Claims, 33 Drawing Sheets

| STAT. MULTIPLE REGRESS. | REGRESSION SUMMARY FOR DEPENDENT VARIABLE: T1_GM R= .79335523 R²= .62941253 ADJUSTED R²= .60708798 F(5,83)=28.194 p<.00000 STD. ERROR OF ESTIMATE: 204.43 | | | | | |
|---|---|---|---|---|---|---|
| M=89 | BETA | ST. ERR. OF BETA | B | ST. ERR. OF B | t(83) | p-LEVEL |
| INTERCPT | | | 17.9230 | 53.23000 | .33671 | .737187 |
| TCH_13 | 1.99624 | .430106 | .1473 | .03173 | 4.64127 | .000013 |
| CH_5 | .59764 | .198540 | 50.9393 | 16.92229 | 3.01019 | .003458 |
| CH_6 | -.56660 | .197619 | -52.0317 | 18.14751 | -2.86715 | .005248 |
| TCH_15 | -2.46260 | .811315 | -1.9403 | .63925 | -3.03533 | .003209 |
| TCH_17 | 1.23523 | .458337 | 1.4393 | .53406 | 2.69501 | .008518 |

| STAT. MULTIPLE REGRESS. | REGRESSION SUMMARY FOR DEPENDENT VARIABLE: T2S_GM $R= .75776513$ $R^2= .57420800$ ADJUSTED $R^2= .55918004$ $F(3,85)=38.209$ $p<.00000$ STD. ERROR OF ESTIMATE: 205.91 | | | | | |
|---|---|---|---|---|---|---|
| M=89 | BETA | ST. ERR. OF BETA | B | ST. ERR. OF B | t(85) | p-LEVEL |
| INTERCPT | | | -5.00711 | 52.00065 | -.09629 | .923517 |
| TCH_13 | 2.38140 | .444665 | .16705 | .03119 | 5.35550 | .000001 |
| TCH_15 | -3.27450 | .834641 | -2.45346 | .62536 | -3.92325 | .000177 |
| TCH_17 | 1.66064 | .469845 | 1.84006 | .52061 | 3.53444 | .000664 |

| STAT. MULTIPLE REGRESS. | REGRESSION SUMMARY FOR DEPENDENT VARIABLE: T2L_GM $R = .77866233$ $R^2 = .60631502$ ADJUSTED $R^2 = .59242026$ $F(3,85) = 43.636$ $p < .00000$ STD. ERROR OF ESTIMATE: 231.71 | | | | | |
|---|---|---|---|---|---|---|
| M=89 | BETA | ST. ERR. OF BETA | B | ST. ERR. OF B | t(85) | p-LEVEL |
| INTERCPT | | | 29.44856 | 58.75698 | .50119 | .617531 |
| TCH_15 | -4.75337 | 1.018179 | -4.16804 | .89280 | -4.66850 | .000011 |
| CH_17 | 1.47767 | .422335 | 1.91616 | .54766 | 3.49881 | .000746 |
| CH_14 | 4.02102 | .689647 | 3.95108 | .67765 | 5.83055 | .000000 |

| STAT. MULTIPLE REGRESS. | REGRESSION SUMMARY FOR DEPENDENT VARIABLE: LOGT1GM R= .88637572 R2= .78566192 ADJUSTED R2= .76524877 F(8,84)=38.448 p<.00000 STD. ERROR OF ESTIMATE: 32962 | | | | | |
|---|---|---|---|---|---|---|
| M=93 | BETA | ST. ERR. OF BETA | B | ST. ERR. OF B | t(84) | p-LEVEL |
| INTERCPT | | | 2.280407 | .121545 | 18.76185 | .000000 |
| A1010 | -.440941 | .103175 | -.121235 | .028368 | -4.27374 | .000050 |
| A690 | -.346236 | .082829 | -.055948 | .013384 | -4.18013 | .000071 |
| A2310 | .384701 | .116716 | .080447 | .024407 | 3.29603 | .001438 |
| A1460 | -.671002 | .118296 | -.261058 | .046024 | -5.67223 | .000000 |
| A2430 | .478393 | .096519 | .218719 | .044128 | 4.95645 | .000004 |
| A3240 | -.306068 | .111275 | -.057827 | .021024 | -2.75054 | .007285 |
| A820 | .247856 | .098250 | .052412 | .020776 | 2.52272 | .013531 |
| A450 | -.145999 | .061254 | -.029812 | .012508 | -2.38349 | .019404 |

| STAT. MULTIPLE REGRESS. | REGRESSION SUMMARY FOR DEPENDENT VARIABLE: LOGT2SGM<br>R= .96760154 R2= .93625274 ADJUSTED R2= .92383444<br>F(15,77)=75.393 p<.00000 STD. ERROR OF ESTIMATE: 29270 | | | | | |
|---|---|---|---|---|---|---|
| M=93 | BETA | ST. ERR. OF BETA | B | ST. ERR. OF B | t(77) | p-LEVEL |
| INTERCPT |  |  | 1.80465 | .144511 | 12.48801 | .000000 |
| A1010 | -.61082 | .089885 | -.20816 | .030632 | -6.79555 | .000000 |
| A730 | -.55863 | .121789 | -.11485 | .025039 | -4.58689 | .000017 |
| A830 | .40241 | .066275 | .10046 | .016546 | 6.07175 | .000000 |
| A2310 | .25179 | .052177 | .06526 | .013524 | 4.82569 | .000007 |
| A300 | -.27190 | .049807 | -.08191 | .015005 | -5.45903 | .000001 |
| A1460 | -3.66746 | .470686 | -1.76855 | .226977 | -7.79173 | .000000 |
| A1280 | 5.11692 | .996881 | 1.95314 | .380513 | 5.13292 | .000002 |
| A3300 | -.22199 | .049744 | -.05111 | .011452 | -4.46259 | .000027 |
| A330 | .26502 | .050055 | .08276 | .015631 | 5.29446 | .000001 |
| A450 | -.14864 | .036684 | -.03762 | .009284 | -4.05183 | .000120 |
| A740 | .54542 | .130763 | .11863 | .028441 | 4.17104 | .000079 |
| A1690 | 5.00947 | .603076 | 2.63396 | .317094 | 8.30654 | .000000 |
| A1270 | -3.99693 | .953122 | -1.53407 | .365820 | -4.19352 | .000073 |
| A1560 | -2.59734 | .775635 | -1.29312 | .386159 | -3.34867 | .001259 |
| A780 | -.31564 | .103097 | -.06742 | .022022 | -3.06157 | .003031 |

| STAT. MULTIPLE REGRESS. | REGRESSION SUMMARY FOR DEPENDENT VARIABLE: LOGT2LGM R= .92226284 R²= .85056875 ADJUSTED R²= .83633720 F(8,84)=59.766 p<.00000 STD. ERROR OF ESTIMATE: 32732 | | | | | |
|---|---|---|---|---|---|---|
| M=93 | BETA | ST. ERR. OF BETA | B | ST. ERR. OF B | t(84) | p-LEVEL |
| INTERCPT | | | 2.19666 | .112046 | 19.60496 | .000000 |
| A1030 | -.46763 | .145003 | -.15303 | .047451 | -3.22499 | .001795 |
| A780 | -.28000 | .087694 | -.05739 | .017973 | -3.19294 | .001983 |
| A810 | .29089 | .084682 | .07172 | .020879 | 3.43507 | .000923 |
| A1550 | -2.29380 | .466732 | -1.26210 | .256806 | -4.91460 | .000004 |
| A2430 | .33021 | .071464 | .17955 | .038857 | 4.62065 | .000014 |
| A570 | -.20446 | .057148 | -.03944 | .011025 | -3.57778 | .000578 |
| A1290 | .56224 | .135614 | .22373 | .053965 | 4.14589 | .000080 |
| A2170 | 1.31447 | .367817 | .81021 | .226714 | 3.57371 | .000586 |

| STAT. MULTIPLE REGRESS. | REGRESSION SUMMARY FOR DEPENDENT VARIABLE: T1_GM $R = .89171608$ $R^2 = .79515756$ ADJUSTED $R^2 = .79249727$ $F(1,77) = 298.90$ $p < .00000$ STD. ERROR OF ESTIMATE: 141.95 | | | | | |
|---|---|---|---|---|---|---|
| M=79 | BETA | ST. ERR. OF BETA | B | ST. ERR. OF B | t(77) | p-LEVEL |
| INTERCPT API_GRAV | .891716 | .051578 | -530.470 25.679 | 55.13346 1.48531 | -9.62155 17.28869 | .000000 .000000 |

| STAT. MULTIPLE REGRESS. | REGRESSION SUMMARY FOR DEPENDENT VARIABLE: T2S_GM<br>R= .86670778 R²= .75118238 ADJUSTED R²= .74795098<br>F(1,77)=232.46 p<.00000 STD. ERROR OF ESTIMATE: 152.52 | | | | | |
|---|---|---|---|---|---|---|
| M=79 | BETA | ST. ERR. OF BETA | B | ST. ERR. OF B | t(77) | p-LEVEL |
| INTERCPT<br>API_GRAV | .866708 | .056845 | -554.899<br>24.332 | 59.23741<br>1.59587 | -9.36738<br>15.24676 | .000000<br>.000000 |

| STAT. MULTIPLE REGRESS. | REGRESSION SUMMARY FOR DEPENDENT VARIABLE: T2L_GM R= .86705287 R²= .75178068 ADJUSTED R²= .74855705 F(1,77)=233.21 p<.00000 STD. ERROR OF ESTIMATE: 173.76 | | | | | |
|---|---|---|---|---|---|---|
| M=79 | BETA | ST. ERR. OF BETA | B | ST. ERR. OF B | t(77) | p-LEVEL |
| INTERCPT<br>API_GRAV | .867053 | .056777 | -625.648<br>27.765 | 67.48869<br>1.81816 | -9.27041<br>15.27120 | .000000<br>.000000 |

| STAT. MULTIPLE REGRESS. | REGRESSION SUMMARY FOR DEPENDENT VARIABLE: T1_GM $R= .81232306$ $R^2= .65986875$ ADJUSTED $R^2= .65545147$ $F(1,77)=149.38$ $p<.00000$ STD. ERROR OF ESTIMATE: 182.91 | | | | | |
|---|---|---|---|---|---|---|
| M=79 | BETA | ST. ERR. OF BETA | B | ST. ERR. OF B | t(77) | p-LEVEL |
| INTERCPT | | | 146.3631 | 28.19095 | 5.19185 | .000002 |
| RCPOISE | .812323 | .066463 | 648.0568 | 53.02274 | 12.22224 | .000000 |

| STAT. MULTIPLE REGRESS. | REGRESSION SUMMARY FOR DEPENDENT VARIABLE: T2S_GM R= .78150832 R²= .61075526 ADJUSTED R²= .60570013 F(1,77)=120.82 p<.00000 STD. ERROR OF ESTIMATE: 190.76 | | | | | |
| --- | --- | --- | --- | --- | --- | --- |
| M=79 | BETA | ST. ERR. OF BETA | B | ST. ERR. OF B | t(77) | p-LEVEL |
| INTERCPT RCPOISE | .781508 | .071099 | 88.6950 607.8103 | 29.40005 55.29686 | 3.01683 10.99177 | .003461 .000000 |

| STAT. MULTIPLE REGRESS. | REGRESSION SUMMARY FOR DEPENDENT VARIABLE: T2L_GM<br>$R = .79393503$ $R^2 = .63033283$ ADJUSTED $R^2 = .62553196$<br>$F(1,77) = 131.30$ $p < .00000$ STD. ERROR OF ESTIMATE: 212.05 | | | | | |
|---|---|---|---|---|---|---|
| M=79 | BETA | ST. ERR. OF BETA | B | ST. ERR. OF B | t(77) | p-LEVEL |
| INTERCPT | | | 104.8641 | 32.68134 | 3.20868 | .001944 |
| RCPOISE | .793935 | .069288 | 704.3315 | 61.46844 | 11.45842 | .000000 |

| STAT. MULTIPLE REGRESS. | REGRESSION SUMMARY FOR DEPENDENT VARIABLE: T1_GM $R= .73332842$ $R^2= .53777058$ ADJUSTED $R^2= .50611103$ $F(5,73)=16.986$ $p<.00000$ STD. ERROR OF ESTIMATE: 219.00 | | | | | |
|---|---|---|---|---|---|---|
| M=79 | BETA | ST. ERR. OF BETA | B | ST. ERR. OF B | t(73) | p-LEVEL |
| INTERCPT | | | 360.80 | 42.046 | 8.58106 | .000000 |
| FL395 | 2.46899 | .544422 | 766.40 | 168.994 | 4.53506 | .000022 |
| FL535 | 1.20748 | .233916 | 482.08 | 63.389 | 5.16204 | .000002 |
| FL710 | -.78859 | .163755 | -6807.52 | 1413.614 | -4.81568 | .000008 |
| FL390 | -1.45853 | .529561 | -582.35 | 211.441 | -2.75421 | .007421 |
| FL475 | -1.12771 | .250558 | -234.05 | 52.002 | -4.50078 | .000025 |

| STAT. MULTIPLE REGRESS. | REGRESSION SUMMARY FOR DEPENDENT VARIABLE: T2S_GM R= .75209603 R²= .56564844 ADJUSTED R²= .53589833 F(5,73)=19.013 p<.00000 STD. ERROR OF ESTIMATE: 206.96 | | | | | |
|---|---|---|---|---|---|---|
| M=79 | BETA | ST. ERR. OF BETA | B | ST. ERR. OF B | t(73) | p-LEVEL |
| INTERCPT | | | 279.07 | 39.735 | 7.02326 | .000000 |
| FL395 | 2.93809 | .527749 | 889.10 | 159.703 | 5.56720 | .000000 |
| FL535 | 1.19110 | .226752 | 463.59 | 88.254 | 5.25288 | .000001 |
| FL710 | -.67740 | .158740 | -5700.74 | 1335.897 | -4.26735 | .000059 |
| FL390 | -1.76484 | .513344 | -686.95 | 199.817 | -3.43792 | .000972 |
| FL475 | -1.33879 | .242885 | -270.88 | 49.143 | -5.51203 | .000001 |

| STAT. MULTIPLE REGRESS. | REGRESSION SUMMARY FOR DEPENDENT VARIABLE: T2L_GM $R= .76061860$ $R^2= .57854066$ ADJUSTED $R^2= .54967358$ $F(5,73)=20.042$ $p<.00000$ STD. ERROR OF ESTIMATE: 232.54 | | | | | |
|---|---|---|---|---|---|---|
| M=79 | BETA | ST. ERR. OF BETA | B | ST. ERR. OF B | t(73) | p-LEVEL |
| INTERCPT | | | 331.75 | 44.646 | 7.43073 | .000000 |
| FL395 | 2.75380 | .519858 | 950.55 | 179.444 | 5.29721 | .000001 |
| FL535 | 1.18627 | .223362 | 526.65 | 99.163 | 5.31097 | .000001 |
| FL710 | -.72937 | .156367 | -7001.54 | 1501.025 | -4.66451 | .000014 |
| FL475 | -1.27227 | .239253 | -293.63 | 55.218 | -5.31766 | .000001 |
| FL390 | -1.60824 | .505668 | -714.05 | 224.516 | -3.18042 | .002159 |

| STAT. MULTIPLE REGRESS. | REGRESSION SUMMARY FOR DEPENDENT VARIABLE: T1_GM<br>R= .91597170 R²= .83900415 ADJUSTED R²= .83476741<br>F(2,76)=198.03 p<.00000 STD. ERROR OF ESTIMATE: 126.67 | | | | | |
|---|---|---|---|---|---|---|
| M=79 | BETA | ST. ERR. OF BETA | B | ST. ERR. OF B | t(76) | p-LEVEL |
| INTERCPT<br>API_GRAV<br>RCPOISE | <br>.648578<br>.320878 | <br>.070530<br>.070530 | -374.734<br>18.677<br>255.991 | 59.93537<br>2.03106<br>56.26736 | -6.25230<br>9.19581<br>4.54954 | .000000<br>.000000<br>.000020 |

| STAT. MULTIPLE REGRESS. | REGRESSION SUMMARY FOR DEPENDENT VARIABLE: T2S_GM R= .88754997 R2= .78774495 ADJUSTED R2= .78215930 F(2,76)=141.03 p<.00000 STD. ERROR OF ESTIMATE: 141.79 | | | | | |
|---|---|---|---|---|---|---|
| M=79 | BETA | ST. ERR. OF BETA | B | ST. ERR. OF B | t(76) | p-LEVEL |
| INTERCPT | | | -416.260 | 67.08958 | -6.20453 | .000000 |
| API_GRAV | .644682 | .080983 | 18.099 | 2.27350 | 7.96071 | .000000 |
| RCPOISE | .293015 | .080983 | 227.890 | 62.98374 | 3.61823 | .000532 |

| STAT. MULTIPLE REGRESS. | REGRESSION SUMMARY FOR DEPENDENT VARIABLE: T2L_GM<br>R= .89208742 R²= .79581997 ADJUSTED R²= .79044681<br>F(2,76)=148.11 p<.00000 STD. ERROR OF ESTIMATE: 158.63 | | | | | |
|---|---|---|---|---|---|---|
| M=79 | BETA | ST. ERR. OF BETA | B | ST. ERR. OF B | t(76) | p-LEVEL |
| INTERCPT<br>API_GRAV<br>RCPOISE | <br>.623381<br>.321582 | <br>.079428<br>.079428 | -452.088<br>19.962<br>285.288 | 75.05686<br>2.54349<br>70.46342 | -6.02328<br>7.84842<br>4.04874 | .000000<br>.000000<br>.000123 |

| STAT. MULTIPLE REGRESS. | REGRESSION SUMMARY FOR DEPENDENT VARIABLE: T1_GM R= .90806731 R²= .82458624 ADJUSTED R²= .81756960 F(3,75)=117.52 p<.00000 STD. ERROR OF ESTIMATE: 133.10 | | | | | |
|---|---|---|---|---|---|---|
| M=79 | BETA | ST. ERR. OF BETA | B | ST. ERR. OF B | t(75) | p-LEVEL |
| INTERCPT | | | -417.65 | 61.644 | -6.77517 | .000000 |
| API_GRAV | .814873 | .053115 | 23.47 | 1.530 | 15.34177 | .000000 |
| FL710 | -.428500 | .121137 | -3699.01 | 1045.710 | -3.53732 | .000697 |
| FL575 | .375565 | .119986 | 256.56 | 81.967 | 3.13006 | .002490 |

| STAT. MULTIPLE REGRESS. | REGRESSION SUMMARY FOR DEPENDENT VARIABLE: T2S_GM  R= .88658994 R²= .78604172 ADJUSTED R²= .77748339  F(3,75)=91.845 p<.00000 STD. ERROR OF ESTIMATE: 143.30 | | | | | |
|---|---|---|---|---|---|---|
| M=79 | BETA | ST. ERR. OF BETA | B | ST. ERR. OF B | t(75) | p-LEVEL |
| INTERCPT | | | -478.345 | 59.9465 | -7.97954 | .000000 |
| API_GRAV | .77172 | .063061 | 21.665 | 1.7704 | 12.23770 | .000000 |
| FL395 | 1.59325 | .479243 | 482.135 | 145.0245 | 3.32451 | .001373 |
| FL405 | -1.48782 | .470814 | -332.053 | 105.0764 | -3.16011 | .002275 |

| STAT. MULTIPLE REGRESS. | REGRESSION SUMMARY FOR DEPENDENT VARIABLE: T2L_GM<br>R= .90737062 R²= .82332145 ADJUSTED R²= .8112208<br>F(5,73)=68.036 p<.00000 STD. ERROR OF ESTIMATE: 150.56 | | | | | |
|---|---|---|---|---|---|---|
| M=79 | BETA | ST. ERR. OF BETA | B | ST. ERR. OF B | t(73) | p-LEVEL |
| INTERCPT | | | -387.98 | 74.673 | -5.19566 | .000002 |
| API_GRAV | .68000 | .062108 | 21.78 | 1.989 | 10.94866 | .000000 |
| FL395 | 2.25186 | .532806 | 777.29 | 183.913 | 4.22642 | .000068 |
| FL405 | -2.23427 | .551381 | -568.79 | 140.367 | -4.05214 | .000125 |
| L710 | -.52544 | .129999 | -5043.87 | 1247.906 | -4.04187 | .000130 |
| L560 | .55243 | .153610 | 338.70 | 94.180 | 3.59630 | .000584 |

| STAT. MULTIPLE REGRESS. | REGRESSION SUMMARY FOR DEPENDENT VARIABLE: T1_GM<br>$R = .92642834$  $R^2 = .85826946$  ADJUSTED $R^2 = .85060835$<br>$F(4,74) = 112.03$  $p < .00000$  STD. ERROR OF ESTIMATE: 120.44 ||||||
|---|---|---|---|---|---|---|
| M=79 | BETA | ST. ERR. OF BETA | B | ST. ERR. OF B | t(74) | p-LEVEL |
| INTERCPT | | | -299.12 | 62.5355 | -4.78322 | .000009 |
| API_GRAV | .612710 | .068075 | 17.64 | 1.9604 | 9.00053 | .000000 |
| RCPOISE | .285191 | .068006 | 227.52 | 54.2536 | 4.19364 | .000075 |
| FL710 | -.351199 | .111159 | -3031.71 | 959.5788 | -3.15942 | .002290 |
| FL575 | .306090 | .109836 | 209.10 | 75.0325 | 2.78680 | .006759 |

| STAT. MULTIPLE REGRESS. | REGRESSION SUMMARY FOR DEPENDENT VARIABLE: T2S_GM $R = .90854854$  $R^2 = .82546046$  ADJUSTED $R^2 = .81602589$  $F(4,74) = 87.493$  $p < .00000$  STD. ERROR OF ESTIMATE: 130.30 | | | | | |
|---|---|---|---|---|---|---|
| M=79 | BETA | ST. ERR. OF BETA | B | ST. ERR. OF B | t(74) | p-LEVEL |
| INTERCPT | | | -332.123 | 65.1956 | -5.09426 | .000003 |
| API_GRAV | .54237 | .080221 | 15.226 | 2.2521 | 6.76095 | .000000 |
| RCPOISE | .30533 | .074688 | 237.468 | 58.0878 | 4.08809 | .000109 |
| FL395 | 1.69579 | .436487 | 513.167 | 132.0861 | 3.88509 | .000221 |
| FL405 | -1.60154 | .429004 | -357.432 | 95.7452 | -3.73316 | .000369 |

| STAT. MULTIPLE REGRESS. | REGRESSION SUMMARY FOR DEPENDENT VARIABLE: T2L_GM $R = .91102268$ $R^2 = .82996233$ ADJUSTED $R^2 = .82077111$ $F(4,74) = 90.299$ $p < .00000$ STD. ERROR OF ESTIMATE: 146.70 | | | | | |
|---|---|---|---|---|---|---|
| M=79 | BETA | ST. ERR. OF BETA | B | ST. ERR. OF B | t(74) | p-LEVEL |
| INTERCPT | | | -360.109 | 73.4009 | -4.90606 | .000005 |
| API_GRAV | .51977 | .079180 | 16.645 | 2.5355 | 6.56450 | .000000 |
| RCPOISE | .33077 | .073718 | 293.443 | 65.3986 | 4.48699 | .000026 |
| FL395 | 1.55633 | .430821 | 537.212 | 148.7101 | 3.61248 | .000550 |
| FL405 | -1.44482 | .423435 | -367.813 | 107.7954 | -3.41214 | .001048 |

| STAT. MULTIPLE REGRESS. | REGRESSION SUMMARY FOR DEPENDENT VARIABLE: T1_GM $R = .82212677$ $R^2 = .67589243$ ADJUSTED $R^2 = .64888347$ $F(6,72) = 25.025$ $p < .00000$ STD. ERROR OF ESTIMATE: 184.65 | | | | | |
|---|---|---|---|---|---|---|
| $M = 79$ | BETA | ST. ERR. OF BETA | B | ST. ERR. OF B | $t(72)$ | p-LEVEL |
| INTERCPT | | | 141.61 | 43.0507 | 3.28941 | .001556 |
| TCH_13 | .52141 | .087635 | .04 | .0063 | 5.94981 | .000000 |
| FL395 | 2.12281 | .469032 | 658.94 | 145.5923 | 4.52595 | .000023 |
| FL475 | -.94071 | .212373 | -195.24 | 44.0769 | -4.42952 | .000033 |
| FL535 | .95759 | .284317 | 382.31 | 113.5110 | 3.36805 | .001218 |
| FL390 | -1.41707 | .460337 | -565.80 | 183.8016 | -3.07834 | .002945 |
| FL645 | -.56825 | .230495 | -1284.03 | 520.8358 | -2.46533 | .016074 |

| STAT. MULTIPLE REGRESS. | REGRESSION SUMMARY FOR DEPENDENT VARIABLE: T2S_GM<br>R= .83641542 R²= .69959075 ADJUSTED R²= .67455665<br>F(6,72)=27.946 p<.00000 STD. ERROR OF ESTIMATE: 173.30 | | | | | |
|---|---|---|---|---|---|---|
| M=79 | BETA | ST. ERR. OF BETA | B | ST. ERR. OF B | t(72) | p-LEVEL |
| INTERCPT | | | .47.05 | 36.6335 | 1.28432 | .203146 |
| TCH_13 | .5445 | .078934 | .04 | .0055 | 6.89796 | .000000 |
| FL405 | -4.4616 | 1.375789 | -995.74 | 307.0489 | -3.24294 | .001794 |
| FL440 | -13.4429 | 3.732963 | -2345.30 | 651.2695 | -3.60112 | .000579 |
| FL420 | 13.9511 | 2.971543 | 2533.22 | 539.5665 | 4.69491 | .000012 |
| FL535 | .2431 | .116862 | 94.62 | 45.4840 | 2.08030 | .041057 |
| FL460 | 3.9117 | 1.912443 | 732.93 | 358.3293 | 2.04541 | .044469 |

| STAT. MULTIPLE REGRESS. | REGRESSION SUMMARY FOR DEPENDENT VARIABLE: T2L_GM<br>R= .83747607 R²= .70136616 ADJUSTED R²= .68091179<br>F(5,73)=34.289 p<.00000 STD. ERROR OF ESTIMATE: 195.74 | | | | | |
|---|---|---|---|---|---|---|
| M=79 | BETA | ST. ERR. OF BETA | B | ST. ERR. OF B | t(73) | p-LEVEL |
| INTERCPT | | | 58.06 | 41.1331 | 1.41155 | .162331 |
| TCH_13 | .56818 | .078984 | .05 | .0063 | 7.19353 | .000000 |
| FL395 | 2.33395 | .934372 | 805.63 | 322.5251 | 2.49788 | .014747 |
| FL405 | -8.79974 | 2.220889 | -2240.18 | 565.3798 | -3.96226 | .000171 |
| FL415 | 9.73595 | 2.673589 | 2101.37 | 577.0562 | 3.64153 | .000503 |
| FL440 | -3.15673 | .933863 | -628.21 | 185.8437 | -3.38030 | .001166 |

| STAT. MULTIPLE REGRESS. | REGRESSION SUMMARY FOR DEPENDENT VARIABLE: T1_GM $R = .94381562\ R^2 = .89078793\ ADJUSTED\ R^2 = .88330765$ $F(5,73) = 119.08\ p < .00000\ STD.\ ERROR\ OF\ ESTIMATE: 106.45$ | | | | | |
|---|---|---|---|---|---|---|
| M=79 | BETA | ST. ERR. OF BETA | B | ST. ERR. OF B | t(73) | p-LEVEL |
| INTERCPT | | | -288.120 | 54.68937 | -5.26830 | .000001 |
| API_GRAV | .57618 | .068198 | 16.593 | 1.96391 | 8.44871 | .000000 |
| RCPOISE | .26353 | .060192 | 210.243 | 48.01996 | 4.37824 | .000039 |
| TCH_15 | -2.48475 | .545964 | -1.965 | .43168 | -4.55112 | .000021 |
| TCH_14 | 2.09614 | .386366 | 1.825 | .33647 | 5.42526 | .000001 |
| TCH_17 | .55148 | .219445 | .661 | .26297 | 2.51305 | .014177 |

| STAT. MULTIPLE REGRESS. | REGRESSION SUMMARY FOR DEPENDENT VARIABLE: T2S_GM<br>R= .93267506 R²= .86988278 ADJUSTED R²= .85705432<br>F(7,71)=67.809 p<.00000 STD. ERROR OF ESTIMATE: 114.86 | | | | | |
|---|---|---|---|---|---|---|
| M=79 | BETA | ST. ERR. OF BETA | B | ST. ERR. OF B | t(71) | p-LEVEL |
| INTERCPT | | | -305.993 | 60.10430 | -5.09103 | .000003 |
| API_GRAV | .57256 | .078265 | 16.074 | 2.19718 | 7.31566 | .000000 |
| RCPOISE | .25627 | .070225 | 199.311 | 54.61657 | 3.64928 | .000499 |
| CH_12 | .38947 | .143695 | 77.037 | 28.42284 | 2.71040 | .008420 |
| TCH_13 | .96152 | .190149 | .068 | .01336 | 5.05663 | .000003 |
| TCH_15 | -1.18360 | .231234 | -.912 | .17824 | -5.11861 | .000003 |
| TCH_16 | .35484 | .111167 | 10.282 | 3.22120 | 3.19195 | .002106 |
| CH_10 | -.30238 | .145271 | -47.518 | 22.82847 | -2.08151 | .040994 |

| STAT. MULTIPLE REGRESS. | REGRESSION SUMMARY FOR DEPENDENT VARIABLE: T2L_GM<br>R= .93645345 R2= .87694507 ADJUSTED R2= .86851665<br>F(5,73)=104.05 p<.00000 STD. ERROR OF ESTIMATE: 125.65 | | | | | |
|---|---|---|---|---|---|---|
| M=79 | BETA | ST. ERR. OF BETA | B | ST. ERR. OF B | t(73) | p-LEVEL |
| INTERCPT | | | -320.043 | 63.09135 | -5.07270 | .000003 |
| API_GRAV | .53088 | .072757 | 17.000 | 2.32988 | 7.29660 | .000000 |
| RCPOISE | .26269 | .064295 | 233.040 | 57.03857 | 4.08565 | .000111 |
| TCH_13 | 1.10971 | .181745 | .089 | .01456 | 6.10589 | .000000 |
| TCH_15 | -1.35835 | .219541 | -1.194 | .19303 | -6.18719 | .000000 |
| TCH_16 | .46346 | .102139 | 15.318 | 3.37589 | 4.53754 | .000022 |

METHOD AND APPARATUS FOR ESTIMATING NMR PROPERTIES BY NEAR INFRARED SPECTRA

BACKGROUND OF THE INVENTION

1. Field of the Invention

This present invention relates to predicting nuclear magnetic resonance (NMR) values for a downhole formation fluid sample, and more particularly, relates to predicting NMR decay times, T1 and T2 for a hydrocarbon sample by employing measured near infrared spectra and predetermined correlations between near infrared spectra and NMR values.

2. Summary of Related Art

The measurement of near infrared (NIR) spectra is well known in the art. See for example, U.S. Pat. No. 5,939,717, by Mullins, entitled "Method and Apparatus for Determining Gas-Oil Ratio in a Geological Formation Through the Use of Spectroscopy", incorporated herein by reference. The Mullins patent discloses a method and apparatus for illuminating formation samples with light and determining a gas-oil ratio from the NIR spectra. Earlier, a similar disclosure for using NIR spectra to estimate gas-oil ratio, API gravity, asphaltenes, and other properties was given in application GB 2,217,838A by DiFoggio. Conventional NMR measurement techniques are well known in the art, as taught in U.S. Pat. No. 5,055,787, Kleinberg et al., entitled Borehole Measurements Of NMR Characteristics Of Earth Formation, herein incorporated by reference. Thus, there are numerous tools available in the industry for measurement of properties of oil formations adjacent a wellbore.

As an alternative to specific measurement tools, mathematical techniques can been utilized to predict oil formation properties based on non-specific measurement tools to determine the desired property. Regression analysis is a popular mathematical technique that is frequently useful for correlation between measured values. Regression analysis is useful to build models explaining a dependent variable or variables in terms of a set of independent variables. The mathematical model or correlation is useful for extrapolating into new population sets other than those observed. Extrapolation or prediction can be performed by choosing values of the independent variables for new cases and thereby predicting the most likely value of the dependent variable. For example, one might wish to predict age at death (the dependent variable) on the basis of life habits, genetic characteristics, and physiology (the independent variables).

The basic bivariate linear regression equation is $$Y = a + b(X - X'),$$

Where Y is the dependent variable, a is a constant, b is the regression coefficient of X on Y, the Xs are independent observations, and X' their mean. For example, Y might be height, b the coefficient with which height changes with age, and X the age. The equation is easily extended to multiple independent variables, in which case b would be a row vector, and X and X' column vectors. Nonlinear regression is also possible. Many forms exist, including polynomial, quadratic, and higher order. An example of a polynomial regression equation of the order 3 (cubic) would be $$Y = a + b1(X - X') + b2(X^2 - X'^2) + b2(X^3 - X'^3).$$

Regression analysis is thus used to build models and, as an extension, to allow extrapolation from the model to predict future values of the dependent variable. While the calculations are basically simple, the presence of numerous variables and observations, particlularly if the independent variables are interrelated, can cause the total amount of calculations to be very large. Various methods of regression analysis are well known in the art and are widely available commercially as computer programs for model building and prediction.

There are, however, no known equations for predicting NMR decay times T1 and T2 from NIR spectra. Thus there is a need for a method and apparatus for predicting NMR decay times T1 and T2 from NIR spectra.

SUMMARY OF THE INVENTION

The present invention provides a method and apparatus for developing a correlation between NIR spectra and the Nuclear Magnetic Resonance (NMR) decay times, T1 and T2 for a library of known crude oil samples, and using the correlation and NIR spectral measurements to predict the NMR decay times, T1 and T2 for unknown crude samples extracted from a formation adjacent a well bore. One of the objects of the invention is to measure NIR spectra to predict the NMR decay times, T1 and T2 of crude oils during or immediately after being sampled down hole by a down hole formation tester such as the Baker Atlas Reservation Characterization Instrument (RCI). It is also an object of the present invention to use these predictions of NMR T1 and T2 decay times to improve log interpretation of NMR logs. One of the advantages of the present invention that it enables the use of existing down hole NIR spectrometers in down hole tools such as the RCI tool string, without requiring the additional expense and time to develop and deploy a separate and independent NMR sensor for the RCI tool or some other down hole tool. Thus, the present invention reduces the length and weight of the down hole tool string and the expense and necessity of an additional independent NMR tool.

DETAILED DESCRIPTION OF THE INVENTION

Figure 1:
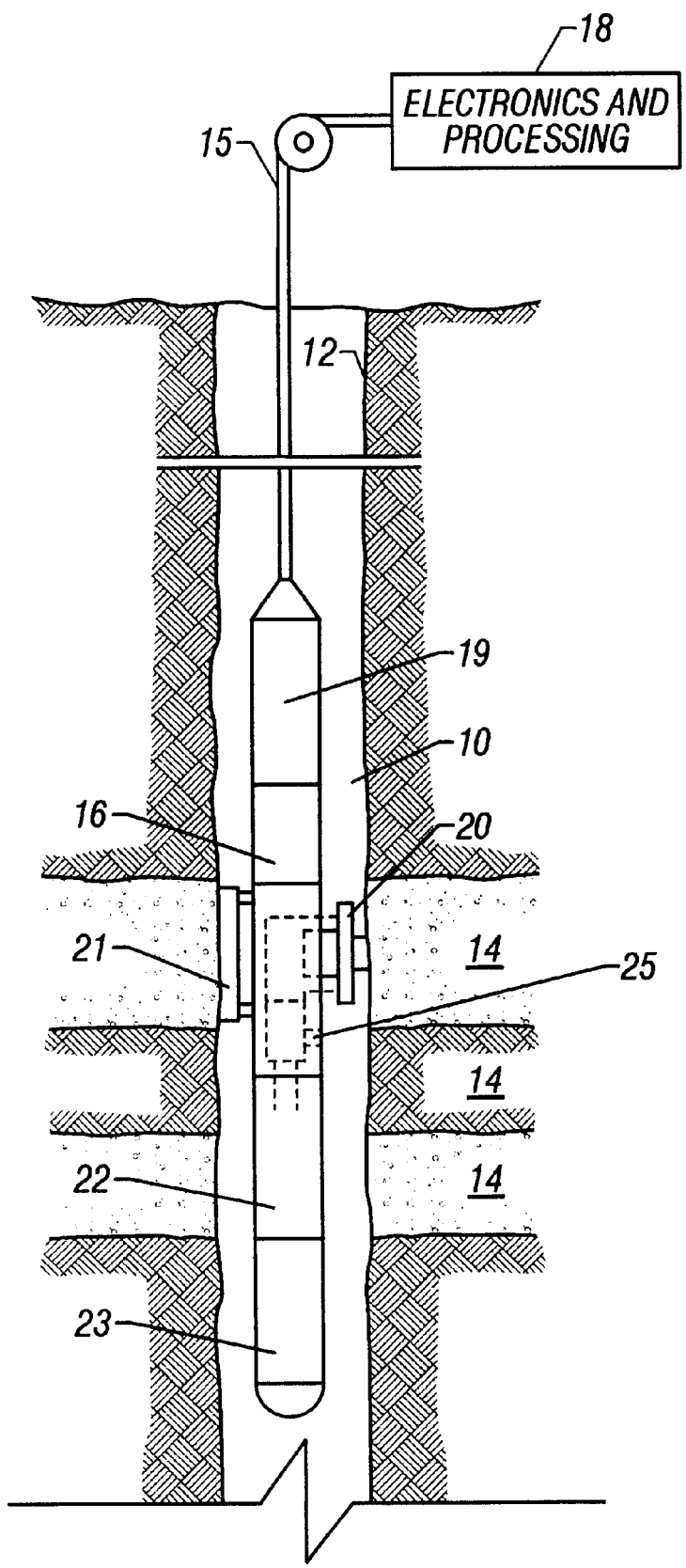
FIG. 1 is an illustration of a conventional NIR tool deployed in a borehole.
Figure 2:
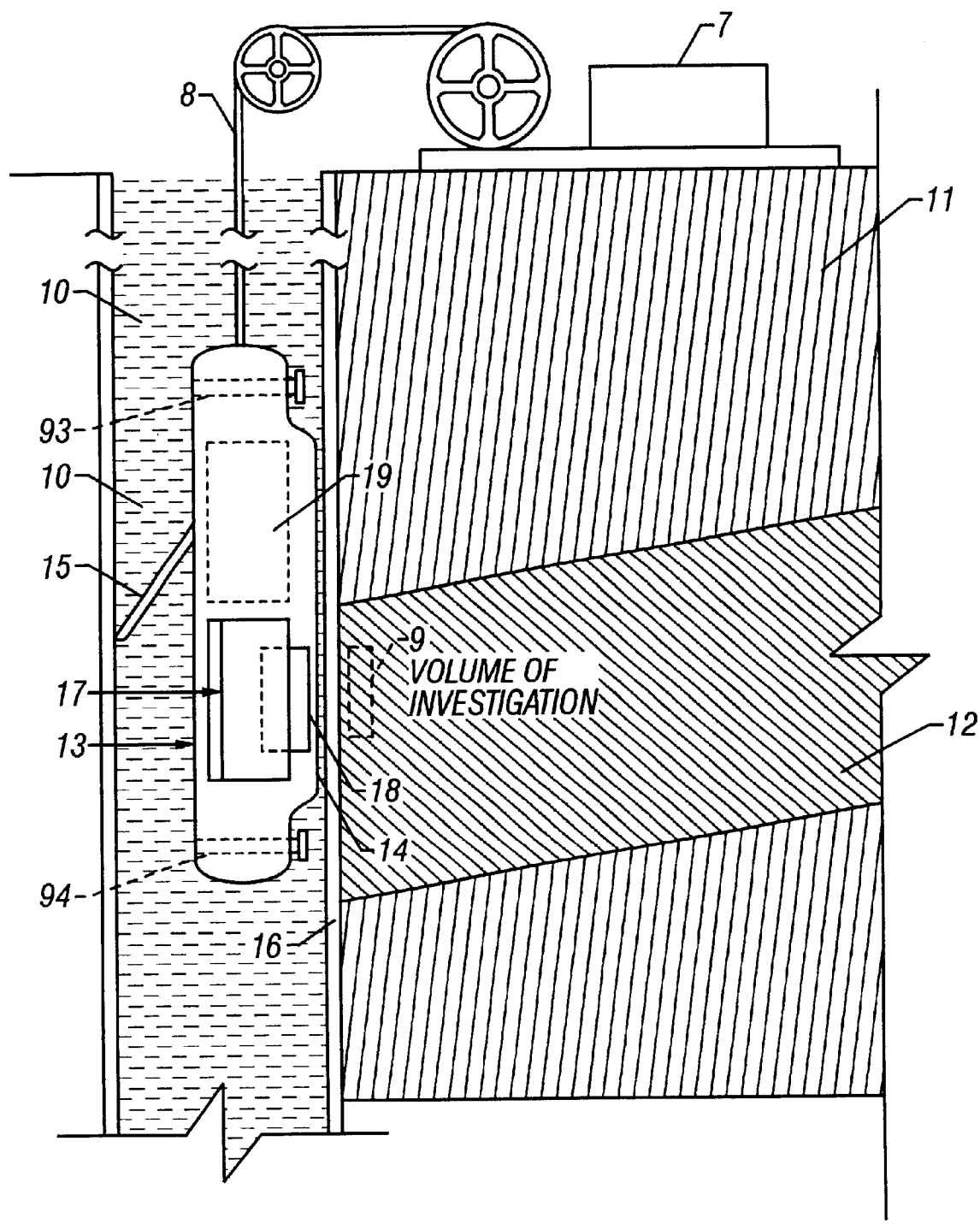
FIG. 2 is an illustration of a conventional NMR tool deployed in a borehole.
Figure 3:
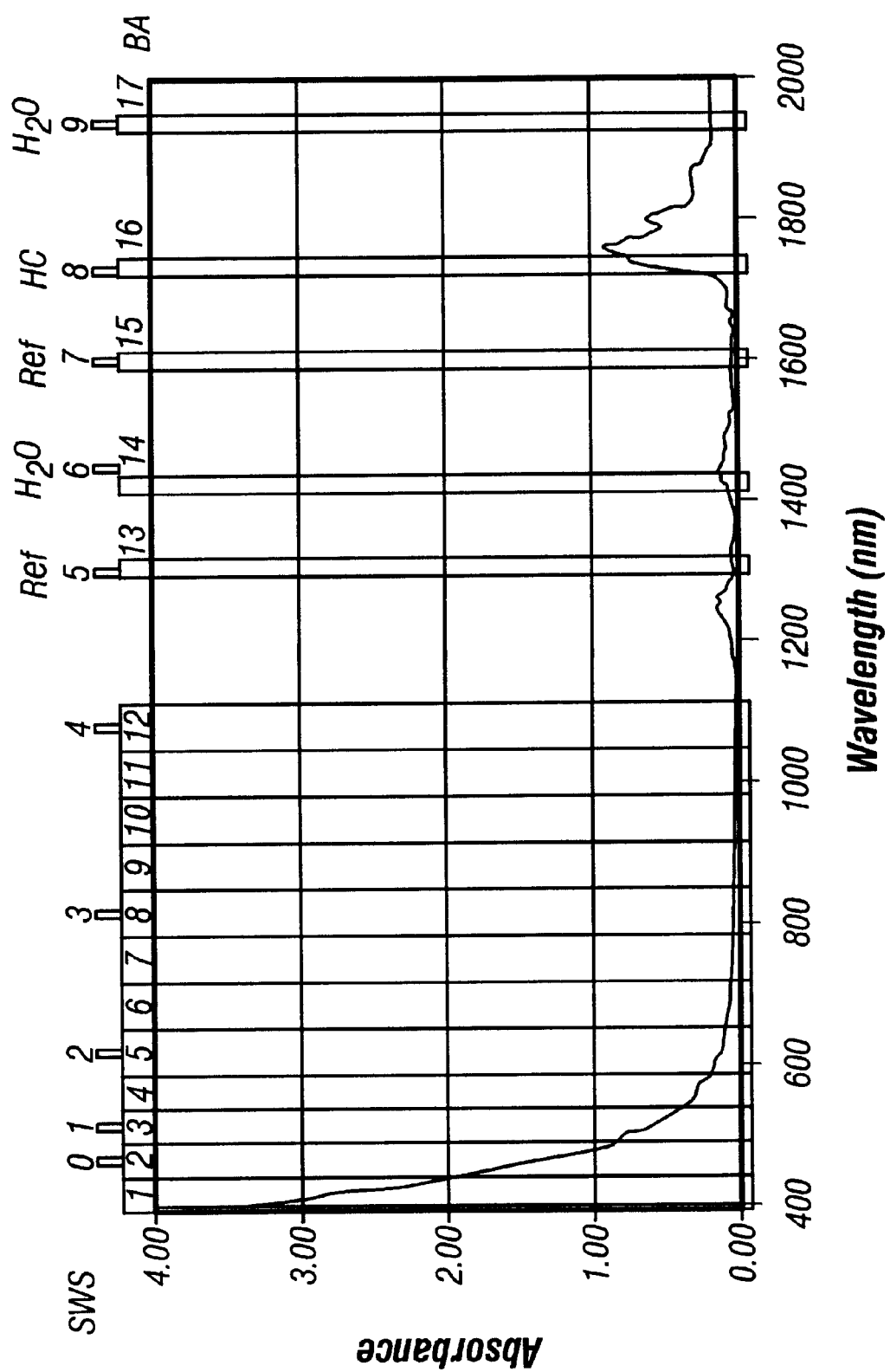
FIG. 3 is an illustration of the NIR channels utilized in a preferred embodiment.

FIG. 1 is an illustration of a conventional NIR tool deployed in a borehole. The operation of the conventional NIR tool shown in FIG. 1 is explained in U.S. Pat. No. 5,939,717. FIG. 2 is an illustration of a conventional NMR tool deployed in a borehole. The operation of the conventional NMR tool shown in FIG. 2 is explained in U.S. Pat. No. 5,055,787. Turning now to FIG. 3, in a preferred embodiment of the present invention, 17 channels of near infrared radiation are sampled and stored to estimate the NMR decay times T1 and T2 for an NIR illuminated down hole sample. The 17 channels range in wavelength as shown in FIG. 3, from 400 to 2,000 nanometers. The method and apparatus of the present invention employs a laboratory quality near infrared spectrum analyzer to perform NIR spectral measurements of a number of test samples of materials having a known or measured NMR values for T1 and T2. In a preferred embodiment, 500 samples were collected and for a substantial number of these, NMR decay times and NIR properties were measured. These values were stored in a training set and used to develop correlation's between the measured or known NMR and measured or known NIR values. That is, a small number of samples may have the desired NMR and NIR analyses performed on them to obtain desired properties and thereafter through regression or some other acceptable statistical methodology and transforms of the original data, for example transform of absorbance data to transmittance data, including but not limited to, step forward multiple linear regression, neural networks, principal component regression and partial least squared, a near-infrared correlation is established based upon NIR/NMR measurements for the chosen number of samples. Additional hydrocarbon samples are then tested by a near-infrared analyzer and their NMR decay times, T1 and T2 predicted from the correlation.

The resulting NIR spectral measurements are stored together with the known corresponding NMR values. A linear regression analysis, or one of the other aforementioned mathematical techniques is used to determine a set of weighting or correlation coefficients and significant near infrared wavelengths that best match portions of the measured near infrared spectra to the known NMR values. These weighting coefficients and wavelengths are then verified by using a further set of samples whose NMR values are known but not provided to the computer or the analyzer to verify its determination of wave lengths and weighting factors.

Regression analysis is well known in the art. The aforementioned mathematical regression techniques are commercially available as software computer programs such as Statistica® available from StatSoft, 2300 E. $14^{th}$ St. Tulsa, Okla. 74103, www.statsoft.com and grams/32® available from Galactic Industries Corporation, 395 Main Street, Salem, N.H. 03079, www.galactic.com.

The absorption bands in near infrared spectrum are due to overtones and combinations of the mid-infrared fundamental molecular vibration bands. The energy transmissions are usually between the ground state and the second or third excited vibrational states. Because higher energy transmissions are successively less likely to occur, each overtone is successively weaker in intensity. The energy required to reach a second or third vibrational state is approximately two or three times that needed for the first excited vibrational state. Since the wavelength at absorption is inversely proportional to its energy, the absorption bands for the second and third excited vibrational states occur at about one-half and one-third of the wavelength at the fundamental or first excited state. Although most fundamental modes can have overtones, the most prominent overtone bands observed in the near infrared region are those related to O—H, C—H, and N—H groups. In addition to the simple overtones which are found in the near infrared region, combination bands also occur. These are usually involved with C—H, O—H or N—H stretch plus one or more bending or rocking modes.

The near-infrared analysis is a secondary analytical technique that is referenced to a primary or "laboratory" standard using multivariate regression analysis. For example, in the present invention, the test set of NMR/NR values was developed for a near-infrared spectra of 500 crude oil samples. The Statistica program was then used on a 166 Mhz personal computer to perform a step forward regression analysis to correlate known NMR values with the measured NIR spectra for the training set. The present invention correlates the 17 channels for NIR spectra to the measured NMR values. The more dominant NIR channel correlation's are selected. The present invention, for example, may select a three-wavelength correlation of the form, $$V = C_0 + C_1 * A_1 + C_2 * A_2 + C_3 * A_3 \tag{1}$$

where V is the measured value, $C_0$, $C_1$, $C_2$ and $C_3$ are constants and $A_1$, $A_2$ and $A_3$ are the near-infrared absorbances at three different wavelengths. Transmittance, which is inversely proportional to ten raised to the power of the absorbance can also be used for developing the correlations. Fluouresence may also be measured and used to develop correlations. Thus, portions of the measured near infrared spectra are correlated with the NMR values T1 and T2. Following this correlation these predetermined portions of near infrared spectra from unknown samples are used with the correlation to determine the NMR T1 and T2 decay time values for unknown samples.

In a preferred embodiment, the present invention divides the near infrared spectra into 17 discrete wavelength regions or predetermined portions of the near infrared spectra, although more or less NIR channels can be used. The computer of the present invention is programmed to relate one or more of the 17 channels for known or measured NIR spectra to the known or measured NMR T1 and T2 decay time values and obtain a set of regression coefficients (which is a measure of the goodness of fit) that is close to 1.00.

By developing correlations between the near-infrared spectra (NIR) and the T1 and T2 Nuclear Magnetic Resonance (NMR) decay times of known crude oils, the present invention uses NIR measurements to predict T1 and T2 decay times for unknown crude oils. The purpose of the present invention is to use the NIR measurements and the formerly generated correlations to estimate the NMR parameters of crude oils while they are being sampled downhole by a formation tester. These estimations can be used to improve log interpretation of NMR logs. One of the advantages of the present invention is that it utilizes an existing downhole NIR spectrometer in the RCI tool string to mathematically estimate NMR T1 and T2 decay time values without the additional expense and time required to deploy a separate NMR sensor tool.

When evaluating Nuclear Magnetic Resonance (NMR) logs, it is useful to know the NMR T1 and NMR T2 decay times of the formation fluids. With the Baker Atlas, Reservoir Characterization Instrument (RCI), the RCI samples formation fluids directly. The present invention operates in place of or in addition to a NMR sensor built into the RCI. A separate NMR tool could measure T1 and T2 of formation fluids down hole. The present invention operates to replace or supplement the use of a separate NMR sensor for the RCI. A separate NMR tool requires additional time, effort, and expense to deploy. A separate NMR tool also adds to the length and weight of the down hole tool string. Moreover, the mathematical processes of the present invention can be easily changed to adapt to changing bore hole conditions.

For example, if a well bore contains a high degree of contamination from filtrate (for example 50% contamination) the NIR spectrum of the contaminated crude oil will be very different from the spectrum of the pure crude oil. This concept and its accommodation is discussed in Guidelines for Applying Chemometrics to Spectra: Feasibility and Error Propogation, by Rocco DiFoggio, APPLIED SPECTROSCOPY, pp. 94a–113a, March 2000, Vol. 54/3, and Liquified-Gas Extraction and Near-Infrared Analysis of Core, by Rocco DiFoggio, Society of Core Analysts, $5^{th}$ Annual Technical Conference, Paper #9131, San Antonio, Aug. 20–23, 1991, incorporated herein by reference. The present invention accommodates this spectral change by adjusting the mathematical algorithm to reduce the effects of the contamination on the spectra. For example, certain spectral regions may be less affected by contamination and these regions may be focused upon when predicting the NMR T1 and T2 values for a contaminated sample to reduce the effects of spectral changes caused by the contamination. Additionally, the present invention may artificially introduce contamination of different levels into duplicate sets of calibration or training sets of spectra and regress the original and contaminated spectra sets together as a single calibration or training set. For large calibration or training sets, it is often sufficient to apply the contamination directly to the original spectra without first adding duplicate sets of calibration or training spectra. To the first order, the mixture spectrum equals the sum of the fraction of contamination times the spectrum of the contaminant plus the fraction of crude oil times the spectrum of that crude oil. Derivatives are also utilized in the present invention to eliminate base line shifts caused by contamination.

In a preferred embodiment, the training set for these correlations comprises a subset of the 500 samples of characterized stock tank crude oils from all over the world. More or less samples, however, could be used to develop the correlation coefficients. These reference samples were also tested in the laboratory to determine and record each sample's UV, visible, near-infrared, NMR, and fluorescence spectra. These data are also used to develop correlations between NMR decay values T1 and T2, and API, viscosity and fluorescence spectra. In an alternative embodiment, additional sensors are added to a down hole tool to measure API gravity, viscosity and fluorescence spectra.

The following examples as shown in FIGS. 4 through 33 further illustrate application of the invention. Note that in the figures, T1__GM denotes Geometric Mean of the T1 distribution; T2L__GM denotes the T2 for Long (2.4 millisecond) echo spacing. T2S__GM denotes the T2 for Short (0.6 millisecond) echo spacing.

Figures 4, 4A:
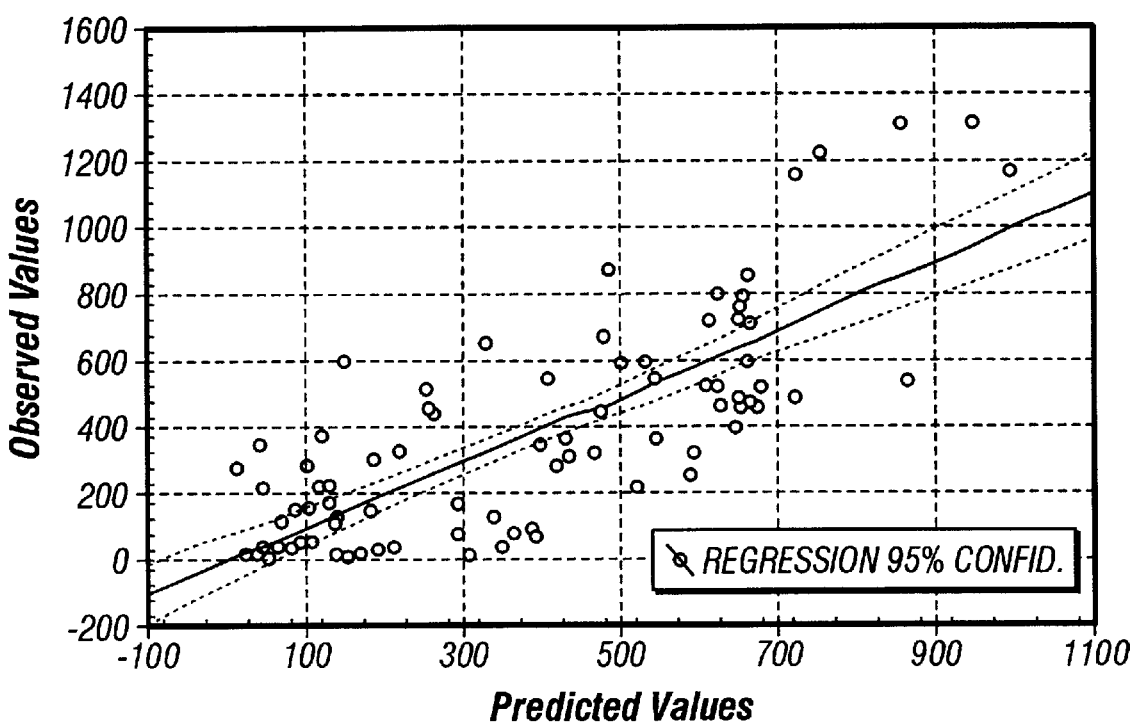
FIGS. 4 and 4A illustrate a regression for dependent variable T1 (geometric mean) in terms of transmittance at channels 13, 15 and 17 and absorbance at channels 5 and 6 in a 17 channel NIR spectrometer.
Figures 5, 5A:
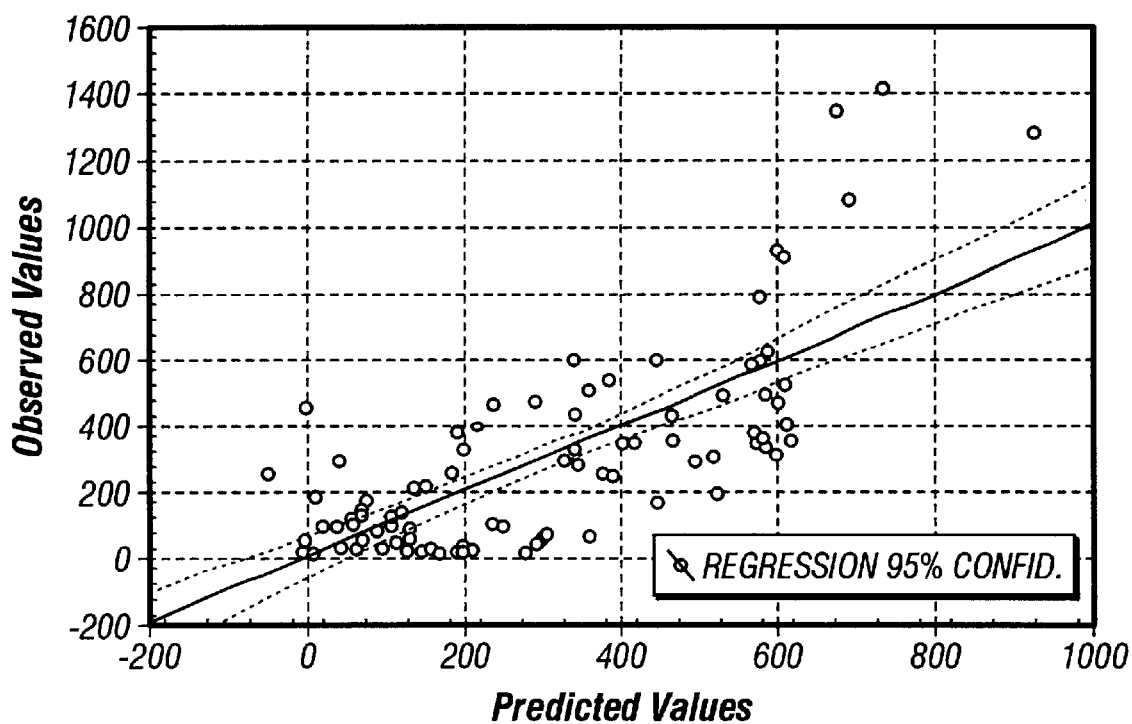
FIGS. 5 and 5A illustrate a regression for dependent variable T2 (geometric mean at 0.6 ms echo spacing) in terms of absorbance at channels 13, 15 and 17 in a 17 channel NIR spectrometer.
Figures 6, 6A:
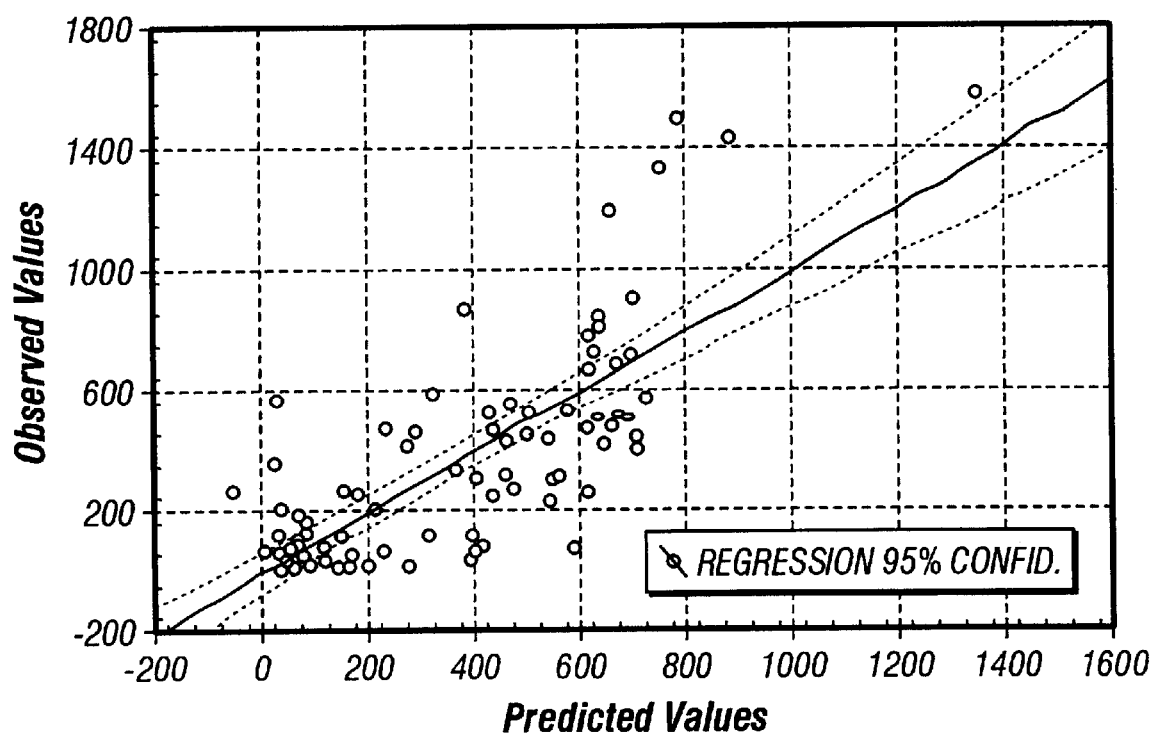
FIGS. 6 and 6A illustrate a regression for dependent variable T2 (geometric mean at 2.4 ms echo spacing) in terms of transmittance at channels 15, 17 and 14 in a 17 channel NIR spectrometer.
Figures 7, 7A:
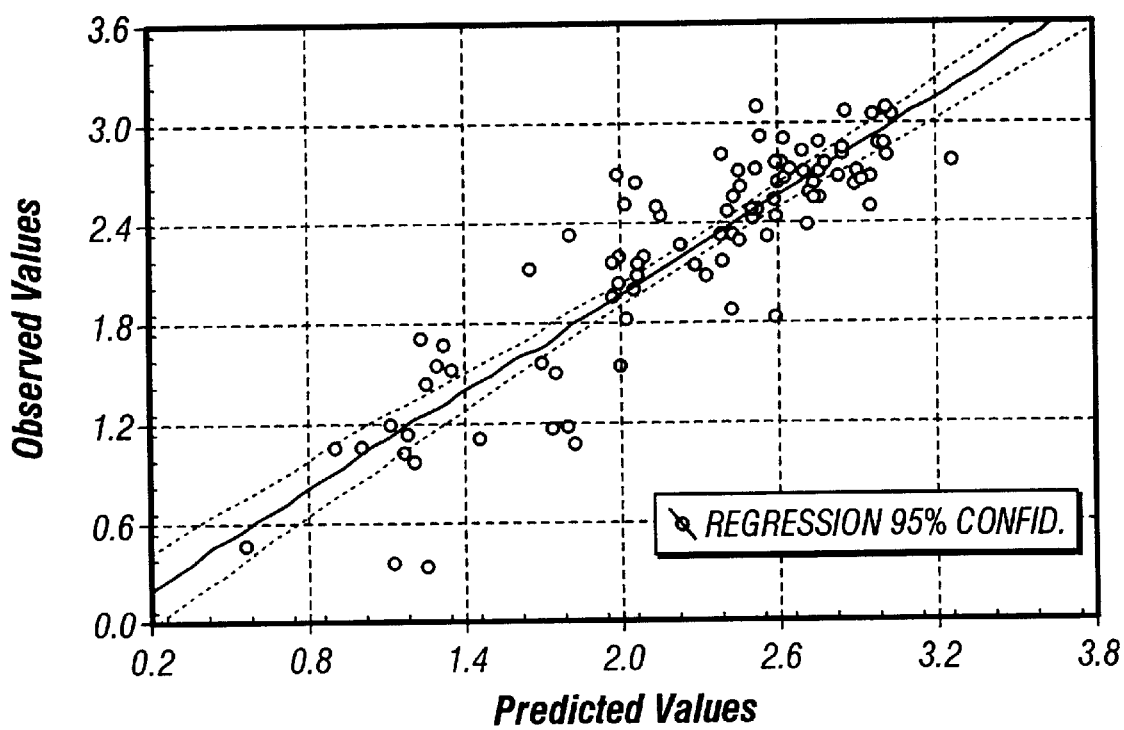
FIGS. 7 and 7A illustrate a regression for dependent variable log T1 (geometric mean) in terms of absorbance at wavelengths 1010, 690, 2310, 1460, 2430, 3240, 820 and 450 nanometers in a 3111 channel/wavelength laboratory NIR spectrometer.

FIGS. 4 and 4A illustrate a regression for dependent variable T1 (geometric mean) in terms of transmittance at channels 13, 15 and 17 and absorbance at channels 5 and 6 in a 17 channel NIR spectrometer. FIGS. 5 and 5A illustrate a regression for dependent variable T2 (geometric mean at 0.6 ms echo spacing) in terms of absorbance at channels 13, 15 and 17 in a 17 channel NIR spectrometer. FIGS. 6 and 6A illustrate a regression for dependent variable T2 (geometric mean at 2.4 ms echo spacing) in terms of transmittance at channels 15, 17 and 14 in a 17 channel NIR spectrometer. FIGS. 7 and 7A illustrate a regression for dependent variable log T1 (geometric mean) in terms of absorbance at wavelengths 1010, 690, 2310, 1460, 2430, 3240, 820 and 450 nanometers in a 3111 channel/wavelength laboratory NIR spectrometer.

Figures 8, 8A:
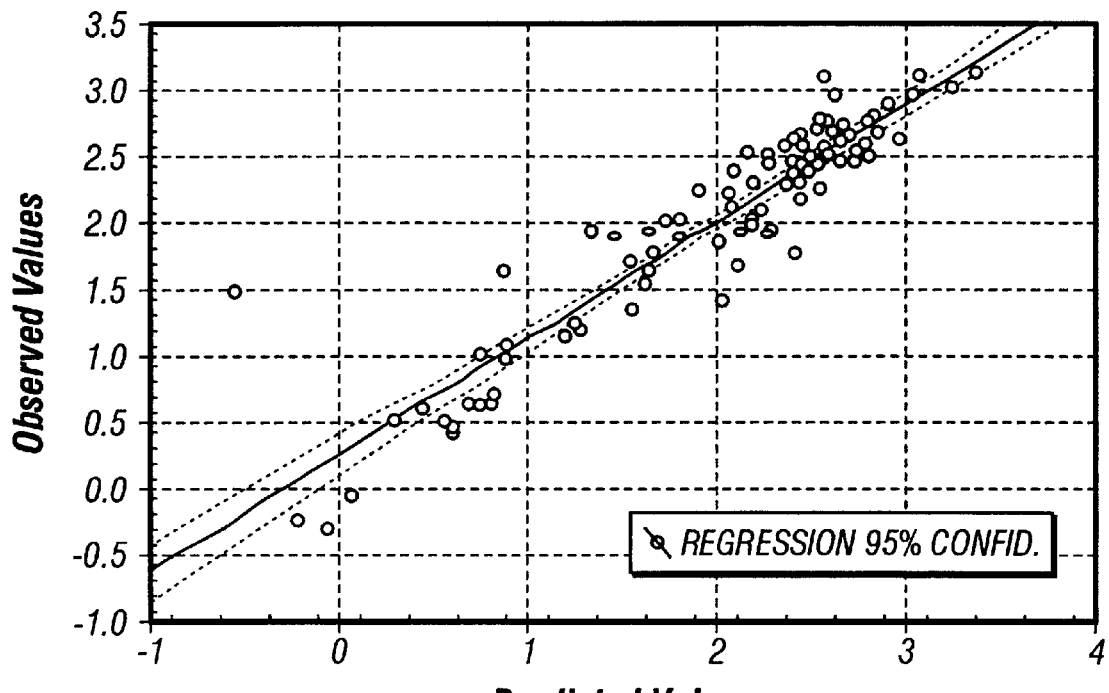
FIGS. 8 and 8A illustrate a regression for dependent variable log T2 (geometric mean at 0.6 ms echo spacing) in terms of absorbance at wavelengths 1010, 730, 830, 2310, 300, 1460, 1280, 3300, 330, 450, 740, 1690, 1270, 1560, and 780 nanometers in a 3111 channel (wavelength) laboratory NIR spectrometer.
Figures 9, 9A:
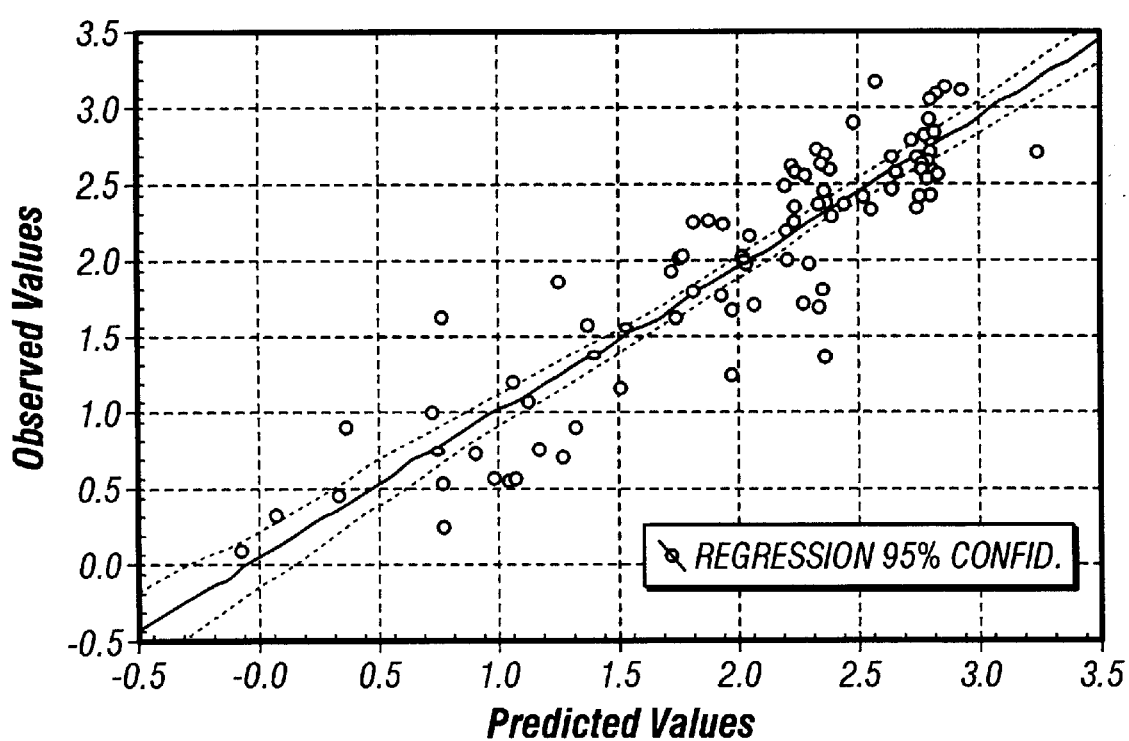
FIGS. 9 and 9A illustrate a regression for dependent variable log T2 (geometric mean at 2.4 ms echo spacing) in terms of absorbance at wavelengths 1030, 780, 810, 1550, 2430, 570, 1290, and 2170 in a 3111 channel (wavelength) laboratory NIR spectrometer.
Figures 10, 10A:
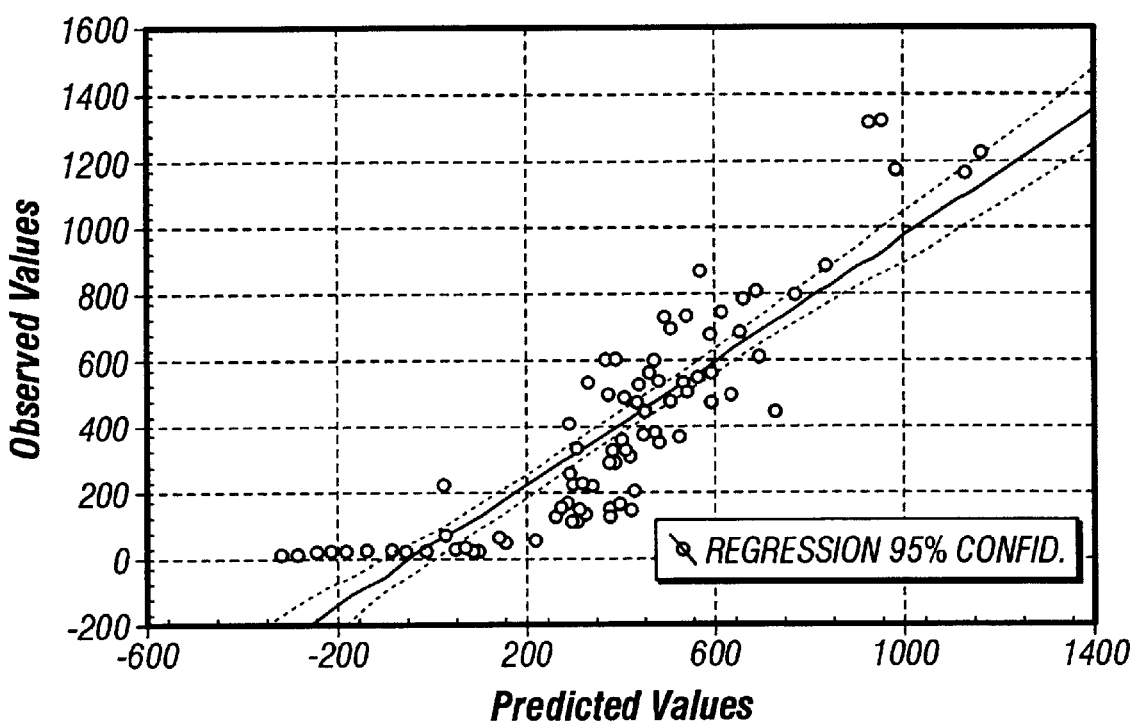
FIGS. 10 and 10A illustrate a regression for dependent variable T1 (geometric mean) in terms of API gravity.
Figures 11, 11A:
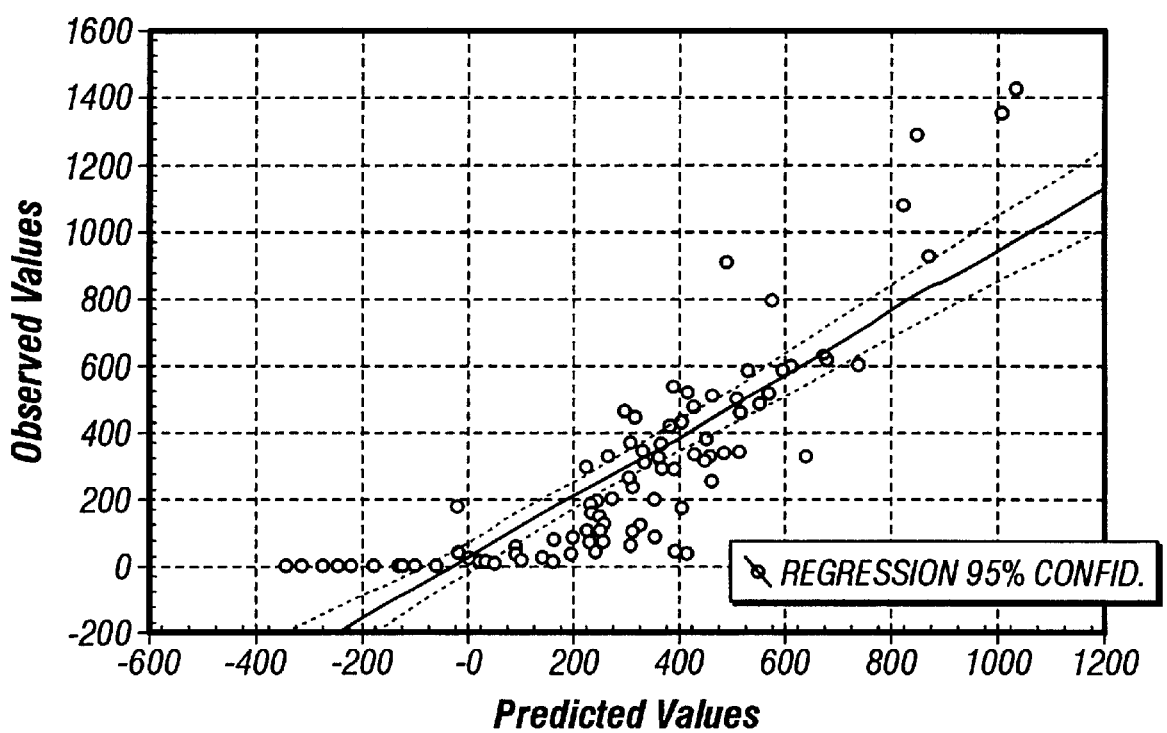
FIGS. 11 and 11A illustrate a regression for dependent variable T2 (geometric mean at 0.6 ms echo spacing) in terms of API gravity.

FIGS. 8 and 8A illustrate a regression for dependent variable log T2 (geometric mean at 0.6 ms echo spacing) in terms of absorbance at wavelengths 1010, 730, 830, 2310, 300, 1460, 1280, 3300, 330, 450, 740, 1690, 1270, 1560, and 780 nanometers in a 3111 channel (wavelength) laboratory NIR spectrometer. FIGS. 9 and 9A illustrate a regression for dependent variable log T2 (geometric mean at 2.4 ms echo spacing) in terms of absorbance at wavelengths 1030, 780, 810, 1550, 2430, 570, 1290, and 2170 in a 3111 channel (wavelength) laboratory NIR spectrometer. FIGS. 10 and 10A illustrate a regression for dependent variable T1 (geometric mean) in terms of API gravity. FIGS. 11 and 11A illustrate a regression for dependent variable T2 (geometric mean at 0.6 ms echo spacing) in terms of API gravity.

Figures 12, 12A:
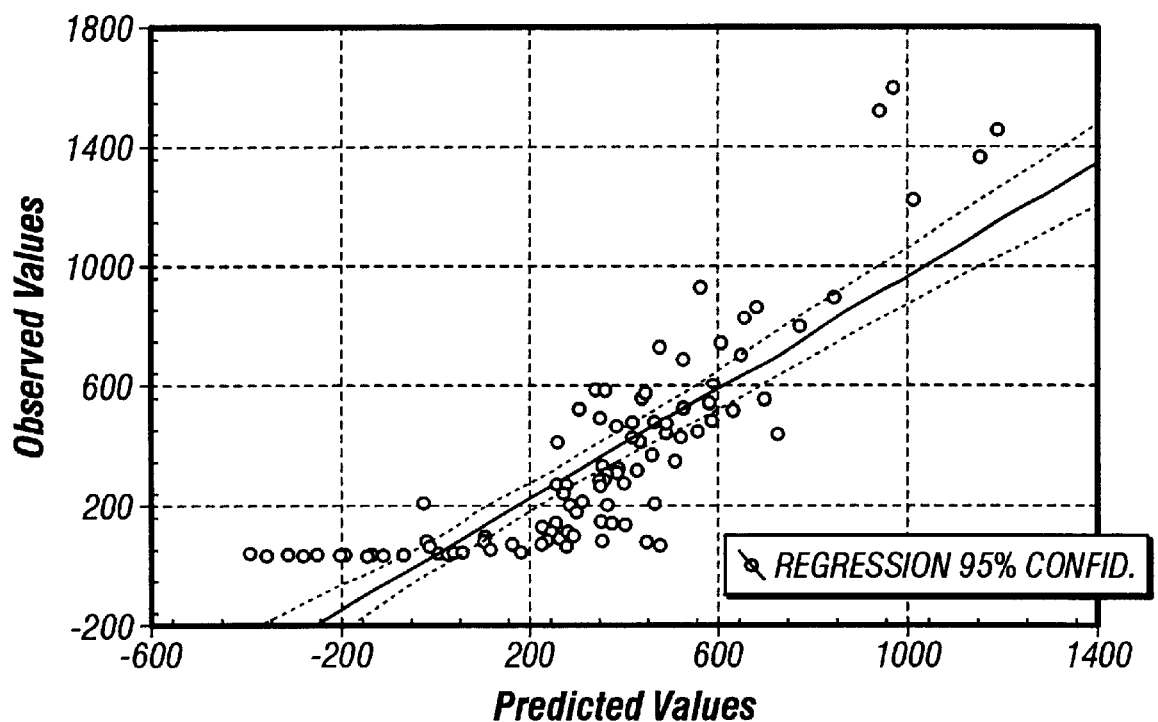
FIGS. 12 and 12A illustrate a regression for dependent variable T2 (geometric mean at 2.4 ms echo spacing) in terms of API gravity.
Figures 13, 13A:
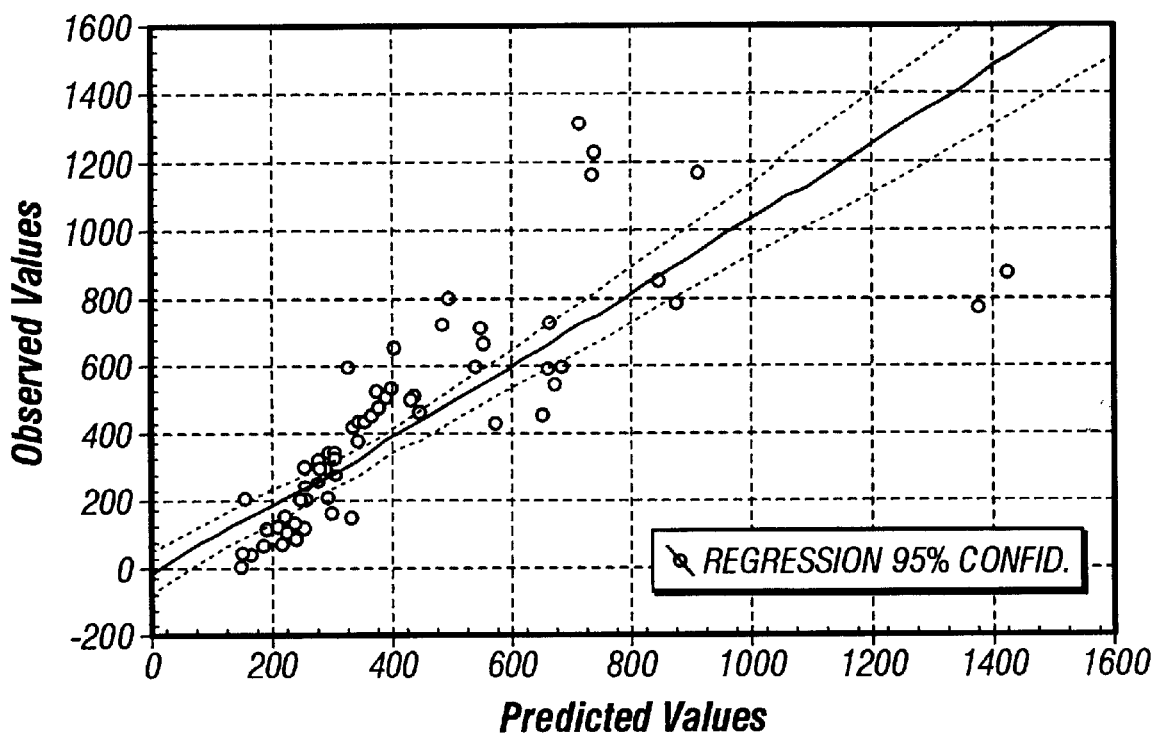
FIGS. 13 and 13A illustrate a regression for dependent variable T1 (geometric mean) in terms of reciprocal viscosity (RCPOISE)
Figures 14, 14A:
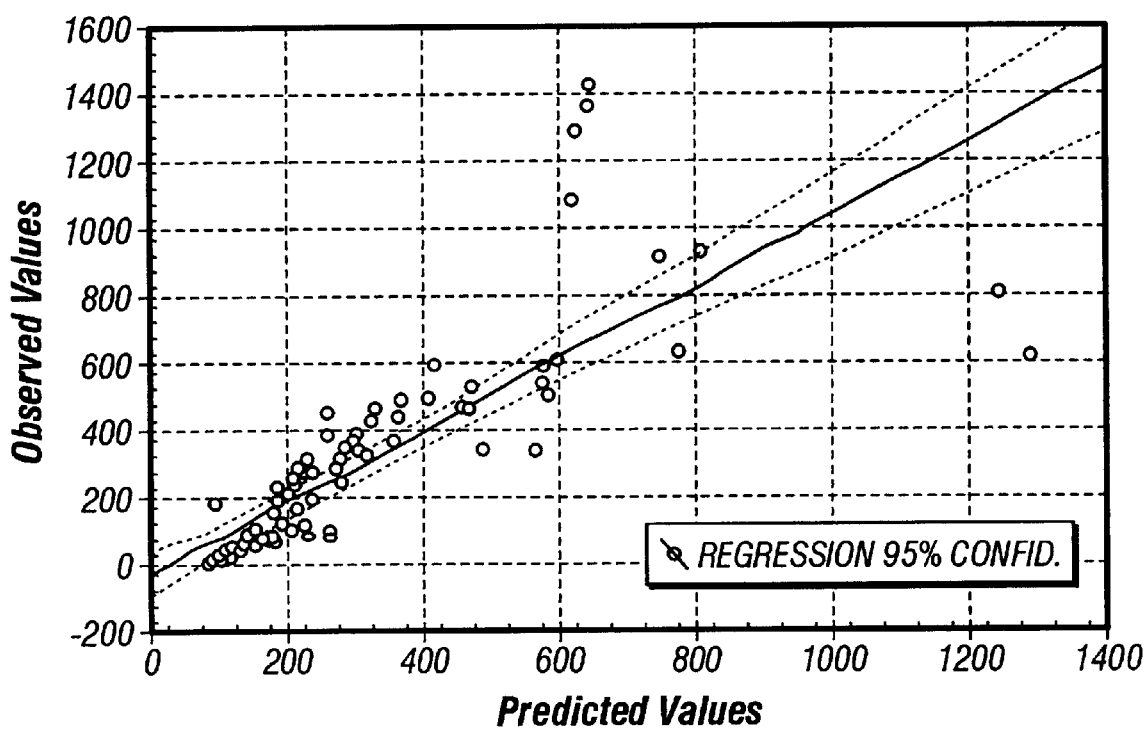
FIGS. 14 and 14A illustrate a regression for dependent variable T2 (geometric mean at 0.6 ms echo spacing) in terms of reciprocal viscosity (RCPOISE)
Figures 15, 15A:
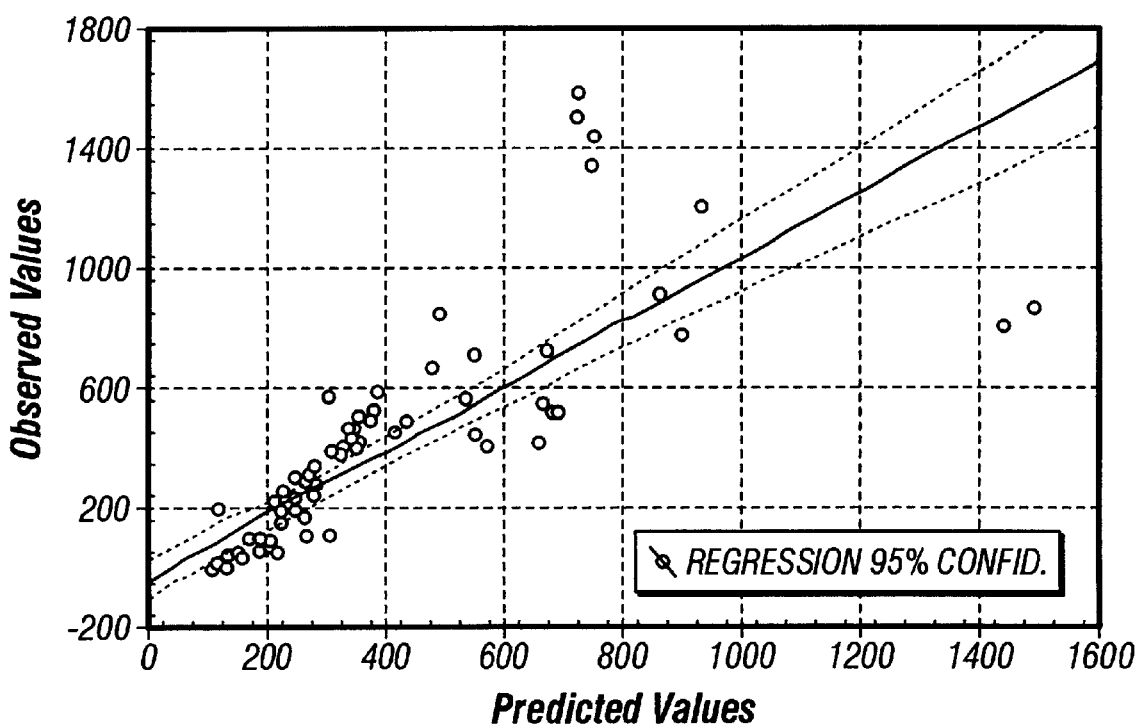
FIGS. 15 and 15A illustrate a regression for dependent variable T2 (geometric mean at 2.4 ms echo spacing) in terms of reciprocal viscosity (RCPOISE)
Figures 16, 16A:
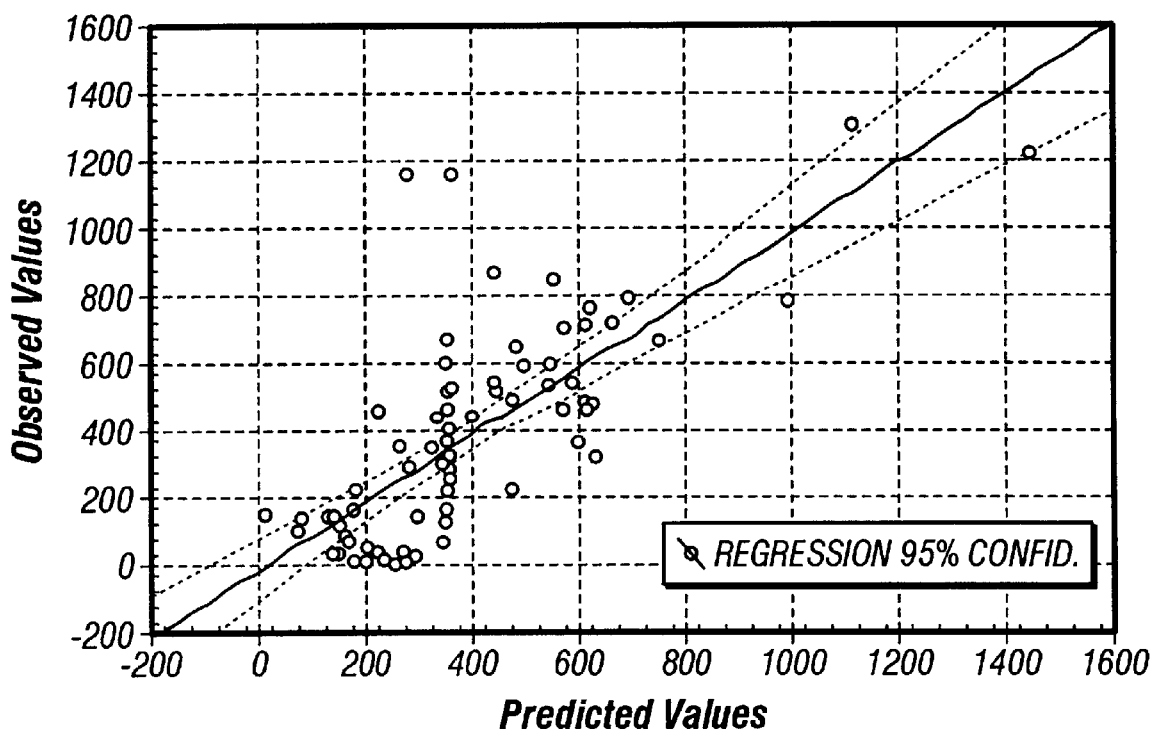
FIGS. 16 and 16A illustrate a regression for dependent variable T1 (geometric mean) in terms of fluorescence at wavelengths at 395, 5353, 710, 390 and 475 nanometers during 360 nm ultraviolet excitation.

FIGS. 12 and 12A illustrate a regression for dependent variable T2 (geometric mean at 2.4 ms echo spacing) in terms of API gravity. FIGS. 13 and 13A illustrate a regression for dependent variable T1 (geometric mean) in terms of reciprocal viscosity (RCPOISE). FIGS. 14 and 14A illustrate a regression for dependent variable T2 (geometric mean at 0.6 ms echo spacing) in terms of reciprocal viscosity (RCPOISE). FIGS. 15 and 15A illustrate a regression for dependent variable T2 (geometric mean at 2.4 ms echo spacing) in terms of reciprocal viscosity (RCPOISE). FIGS. 16 and 16A illustrate a regression for dependent variable T1 (geometric mean) in terms of fluorescence at wavelengths at 395, 5353, 710, 390 and 475 nanometers during 360 nm ultraviolet excitation.

Figures 17, 17A:
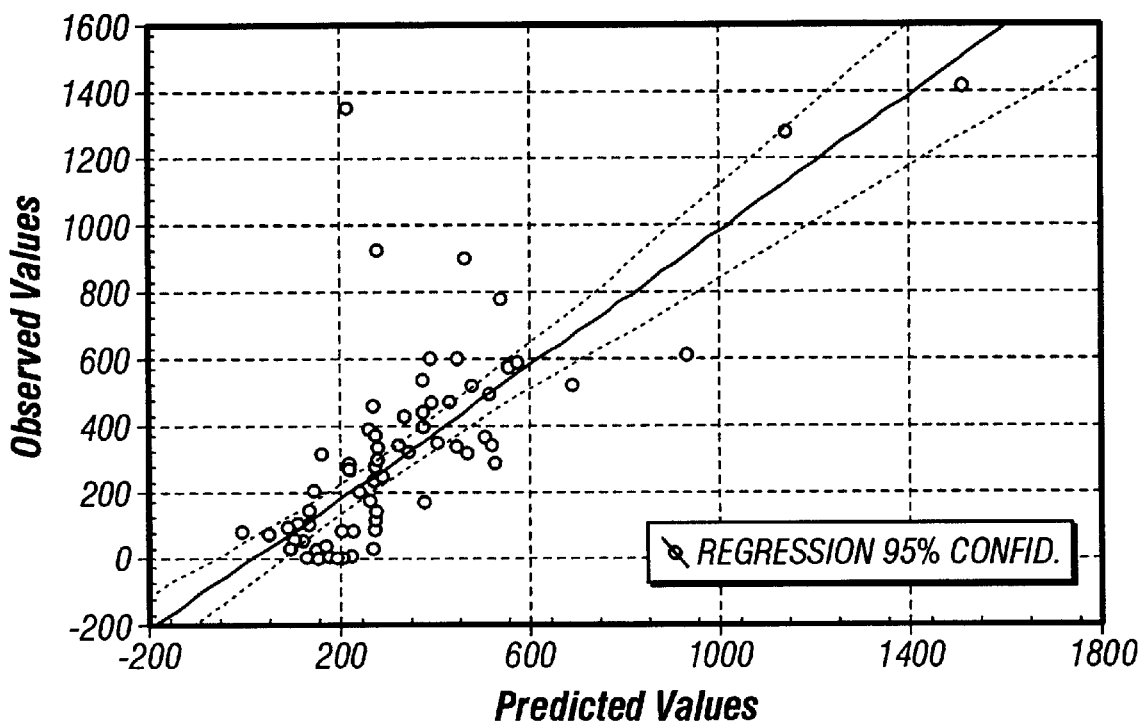
FIGS. 17 and 17A illustrate a regression for dependent variable T2 (geometric mean at 0.6 ms echo spacing) in terms of fluorescence at wavelengths 395, 535, 710, 390 and 475 nanometers during 360 nm ultraviolet excitation.
Figures 18, 18A:
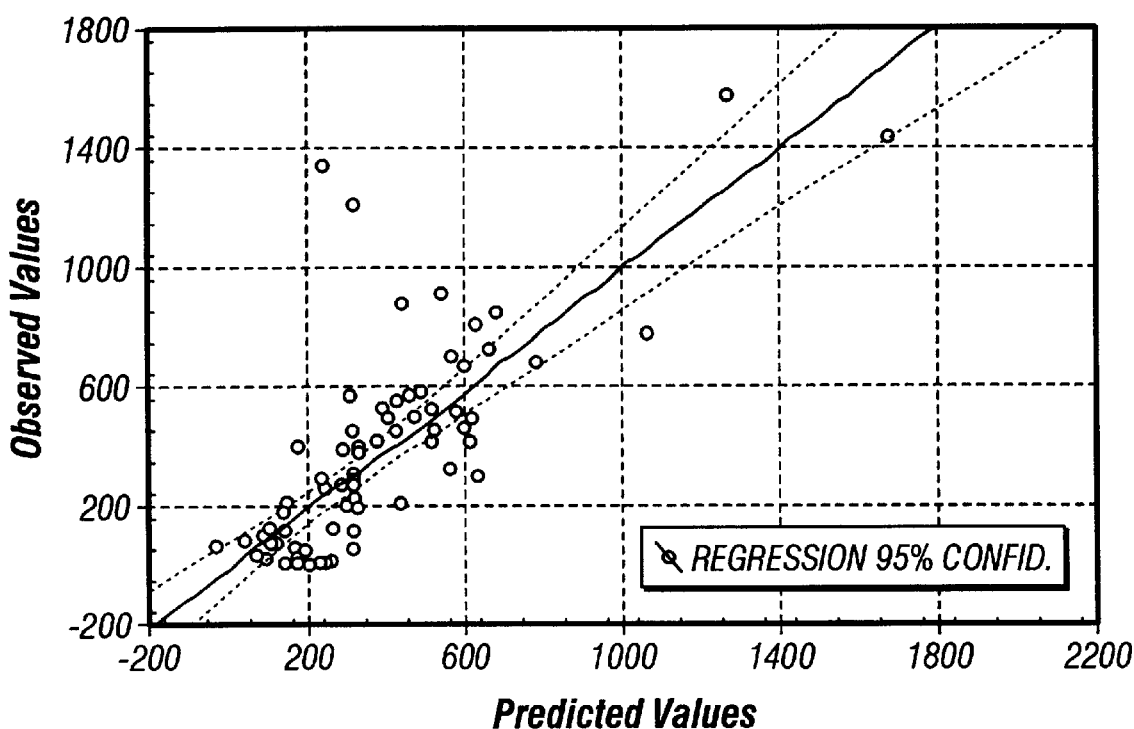
FIGS. 18 and 18A illustrate a regression for dependent variable T2 (geometric mean at 2.4 ms echo spacing) in terms of fluorescence at wavelengths at 395, 535, 710, 390 and 475 nanometers during 360 nm ultraviolent excitation.
Figures 19, 19A:
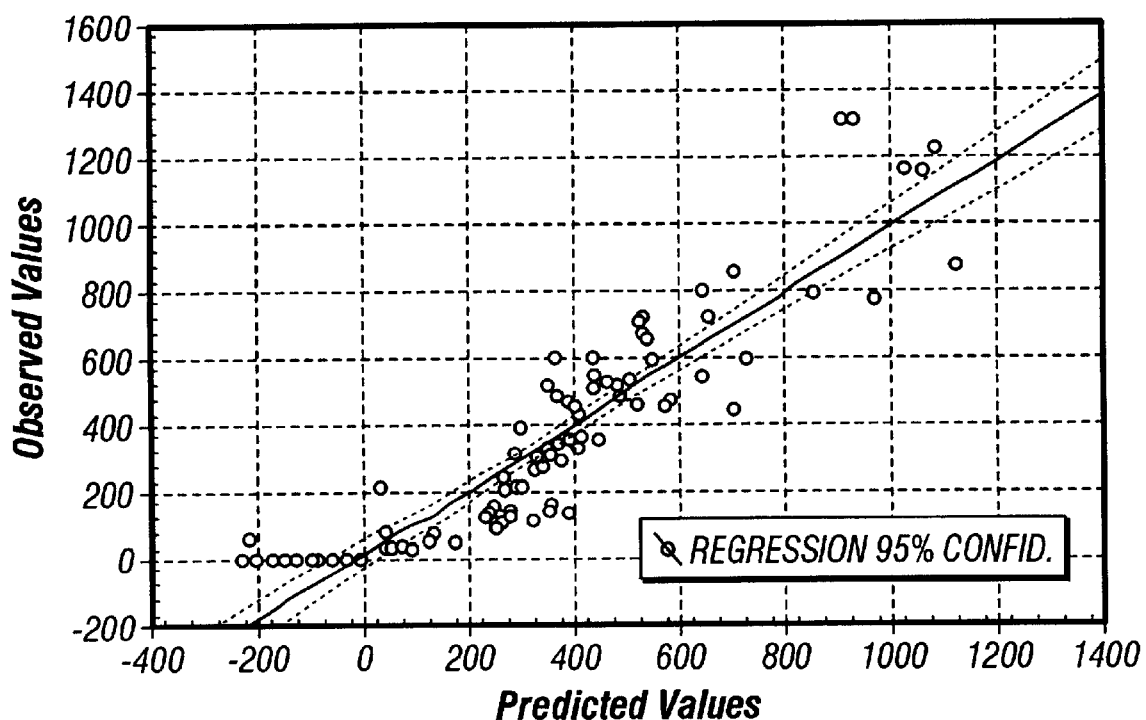
FIGS. 19 and 19A illustrate a regression for dependent variable T1 (geometric mean) in terms of API gravity and reciprocal viscosity (RCPOISE)
Figures 20, 20A:
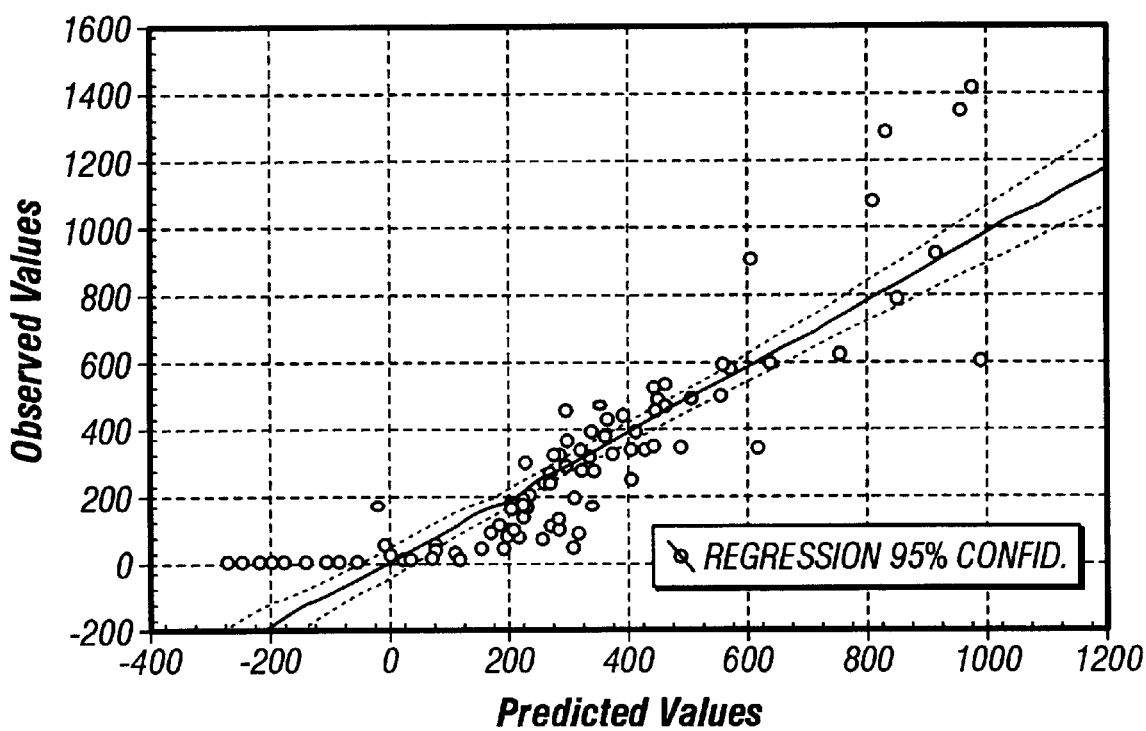
FIGS. 20 and 20A illustrate a regression for dependent variable T2 (geometric mean at 0.6 ms echo spacing) in terms of API gravity and reciprocal viscosity (RCPOISE)
Figures 21, 21A:
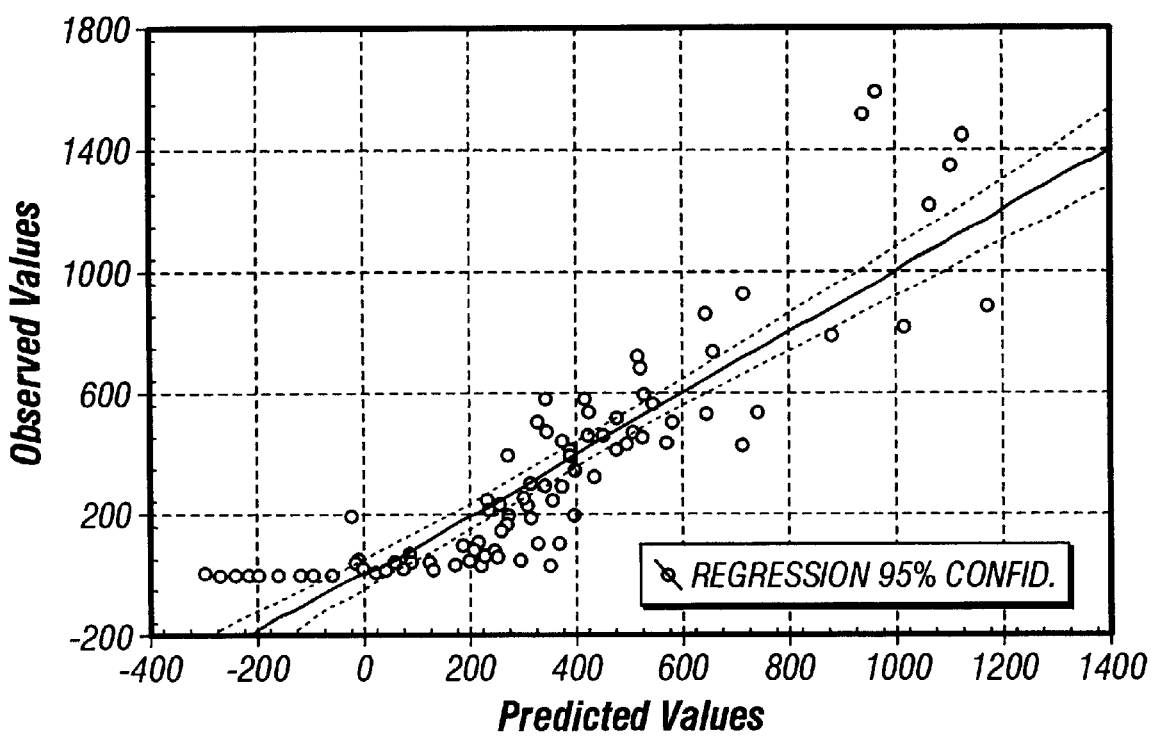
FIGS. 21 and 21A illustrate a regression for dependent variable T2 (geometric mean at 2.4 ms echo spacing) in terms of API gravity and reciprocal viscosity (RCPOISE)

FIGS. 17 and 17A illustrate a regression for dependent variable T2 (geometric mean at 0.6 ms echo spacing) in terms of fluorescence at wavelengths 395, 535, 710, 390 and 475 nanometers during 360 nm ultraviolet excitation. FIGS. 18 and 18A illustrate a regression for dependent variable T2 (geometric mean at 2.4 ms echo spacing) in terms of fluorescence at wavelengths at 395, 535, 710, 390 and 475 nanometers during 360 nm ultraviolent excitation. FIGS. 19 and 19A illustrate a regression for dependent variable T1 (geometric mean) in terms of API gravity and reciprocal viscosity (RCPOISE). FIGS. 20 and 20A illustrate a regression for dependent variable T2 (geometric mean at 0.6 ms echo spacing) in terms of API gravity and reciprocal viscosity (RCPOISE). FIGS. 21 and 21A illustrate a regression for dependent variable T2 (geometric mean at 2.4 ms echo spacing) in terms of API gravity and reciprocal viscosity (RCPOISE).

Figures 22, 22A:
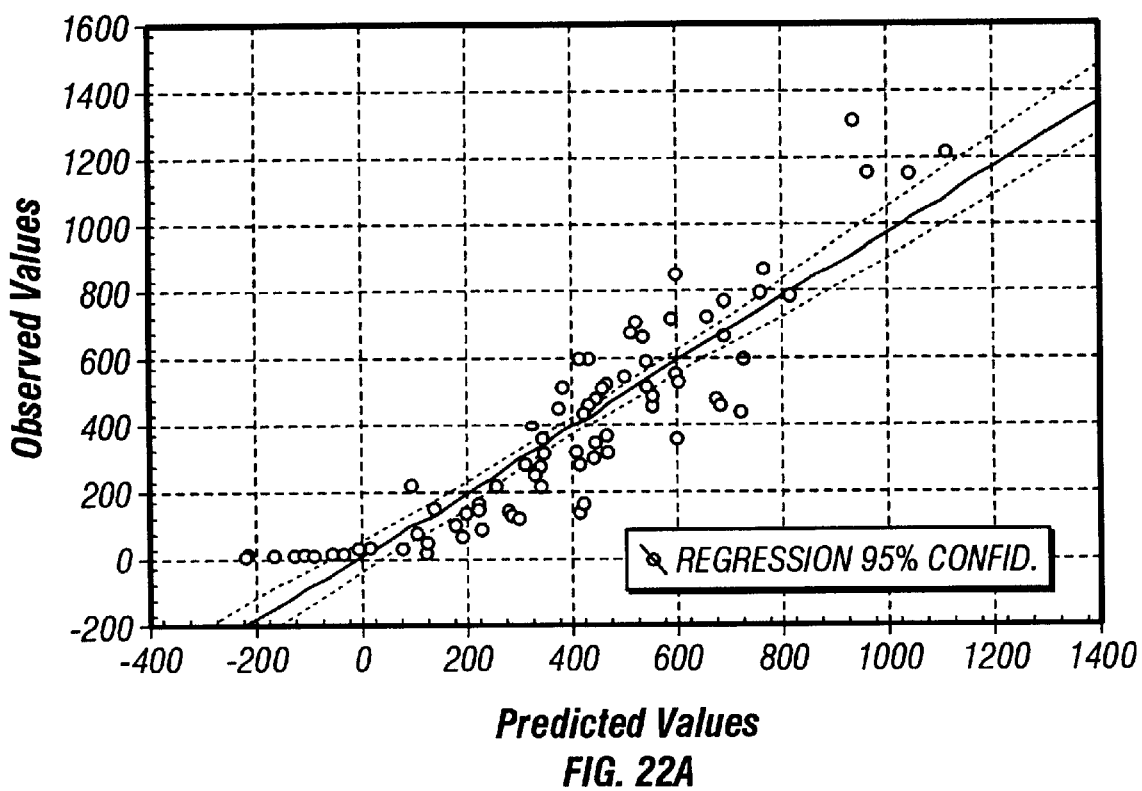
FIGS. 22 and 22A illustrate a regression for dependent variable T1 (geometric mean) in terms of API gravity and fluorescence emission wavelengths at 710 and 575 nanometers during 360 nm ultraviolet excitation.
Figures 23, 23A:
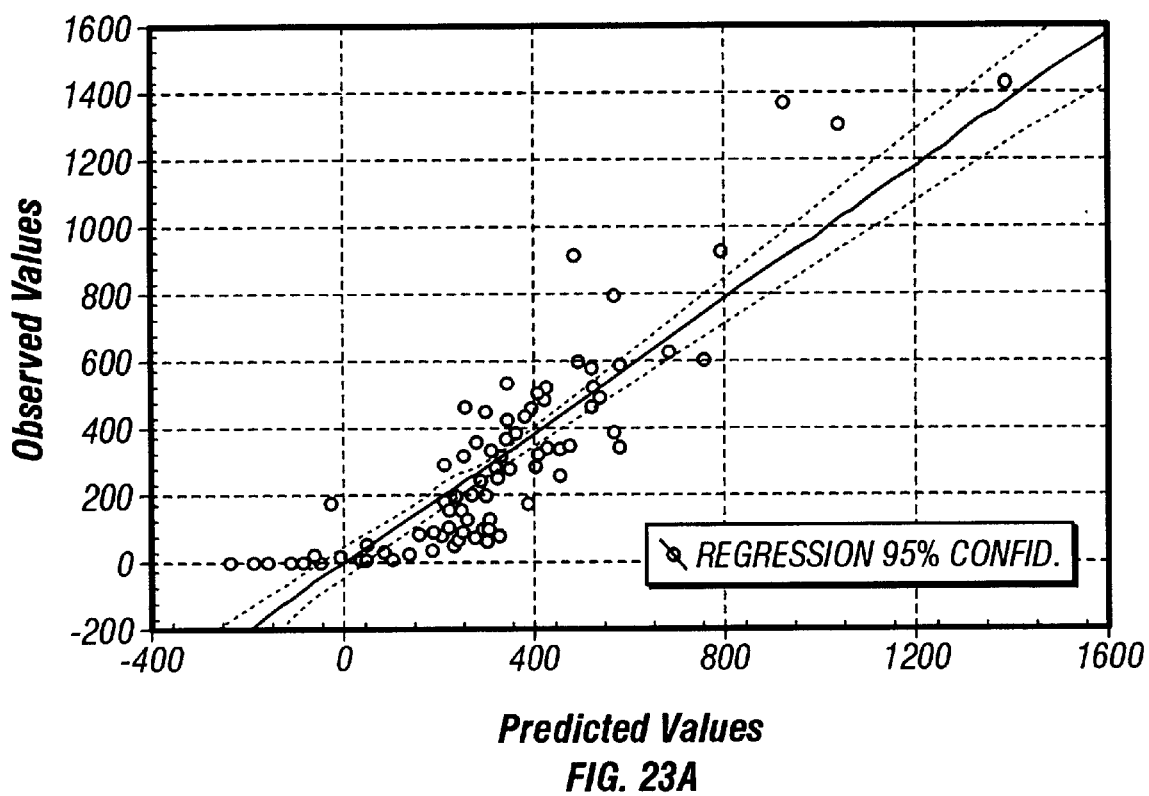
FIGS. 23 and 23A illustrate a regression for dependent variable T2 (geometric mean at 0.6 ms echo spacing) in terms of API gravity and fluorescence emission at wavelengths 395 and 405 nanometers during 360 nm ultraviolet excitation.
Figures 24, 24A:
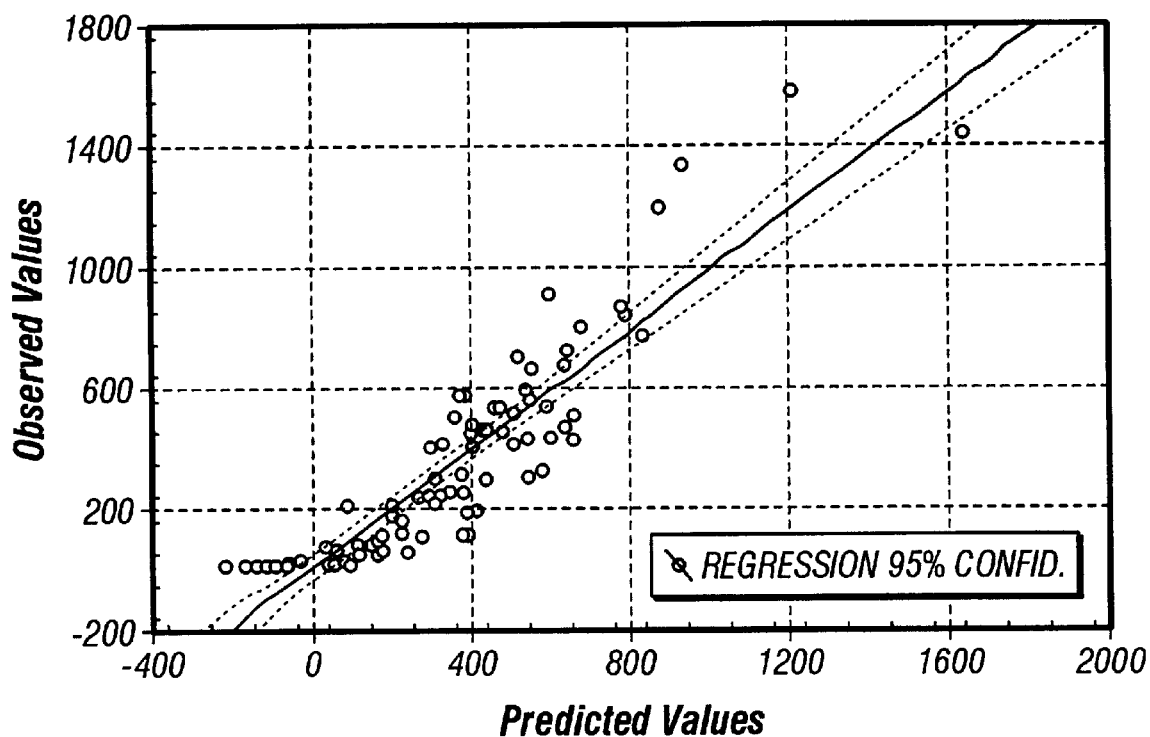
FIGS. 24 and 24A illustrate a regression for dependent variable T2 (geometric mean at 2.4 ms echo spacing) in terms of API gravity and fluorescence emission at wavelengths 395, 405, 710 and 560 nanometers during 360 nm ultraviolent excitation.
Figures 25, 25A:
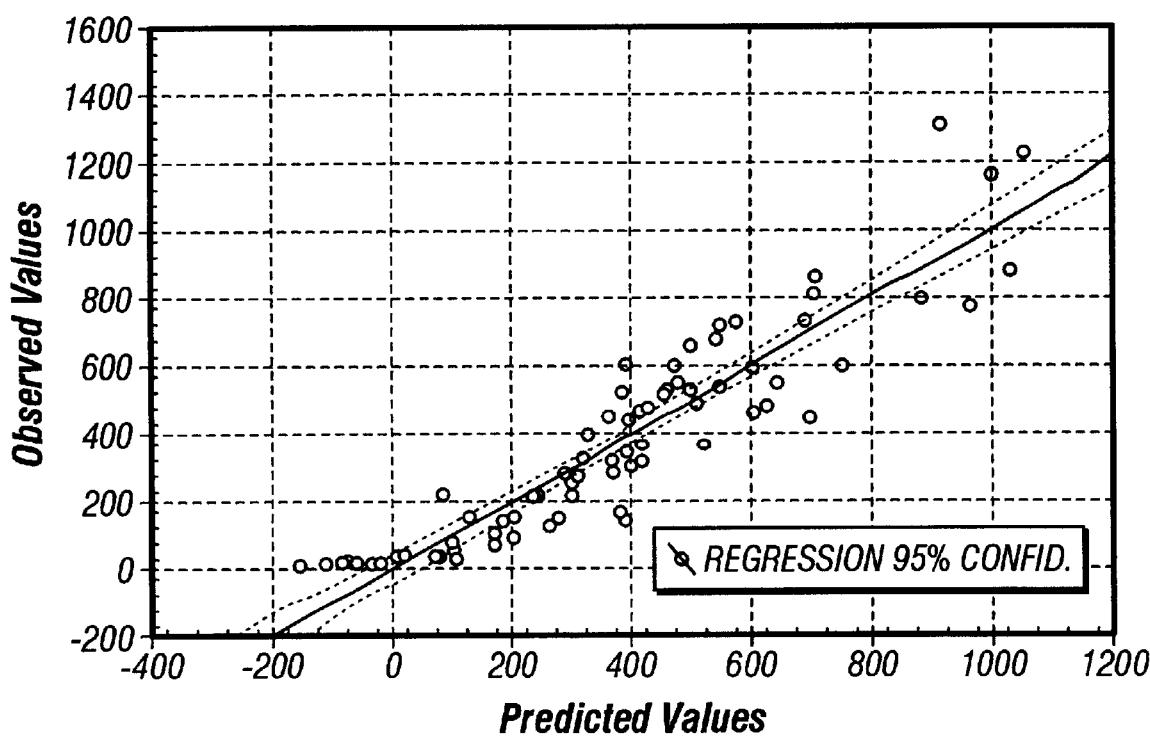
FIGS. 25 and 25A illustrate a regression for dependent variable T1 (geometric mean) in terms of API gravity, reciprocal viscosity and fluorescence at wavelengths 710 and 575 nanometers during 360 nm ultraviolet excitation.

FIGS. 22 and 22A illustrate a regression for dependent variable T1 (geometric mean) in terms of API gravity and fluorescence emission wavelengths at 710 and 575 nanometers during 360 nm ultraviolet excitation. FIGS. 23 and 23A illustrate a regression for dependent variable T2 (geometric mean at 0.6 ms echo spacing) in terms of API gravity and fluorescence emission at wavelengths 395 and 405 nanometers during 360 nm ultraviolent excitation. FIGS. 24 and 24A illustrate a regression for dependent variable T2 (geometric mean at 2.4 ms echo spacing) in terms of API gravity and fluorescence emission at wavelengths 395, 405, 710 and 560 nanometers during 360 nm ultraviolent excitation. FIGS. 25 and 25A illustrate a regression for dependent variable T1 (geometric mean) in terms of API gravity, reciprocal viscosity and fluorescence at wavelengths 710 and 575 nanometers during 360 nm ultraviolet excitation.

Figures 26, 26A:
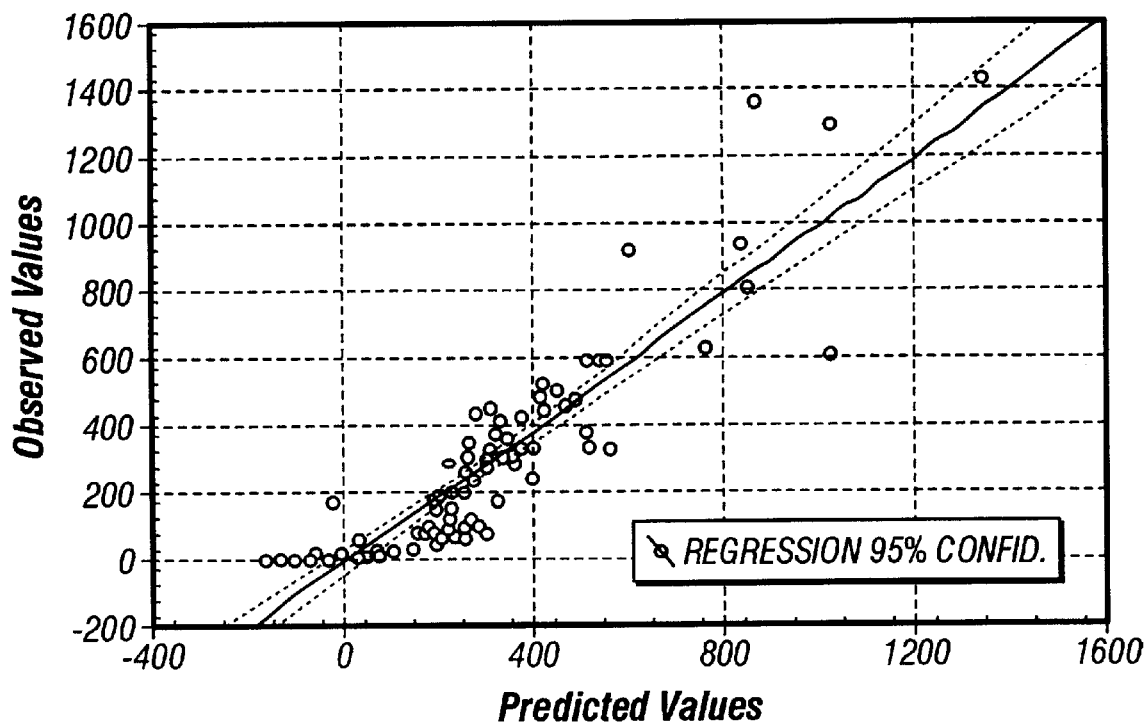
FIGS. 26 and 26A illustrate a regression for dependent variable T2 (geometric mean at 0.6 ms echo spacing) in terms of API gravity, reciprocal viscosity and fluorescence emission at wavelengths 395 and 405 nanometers during 360 nm ultraviolent excitation.
Figures 27, 27A:
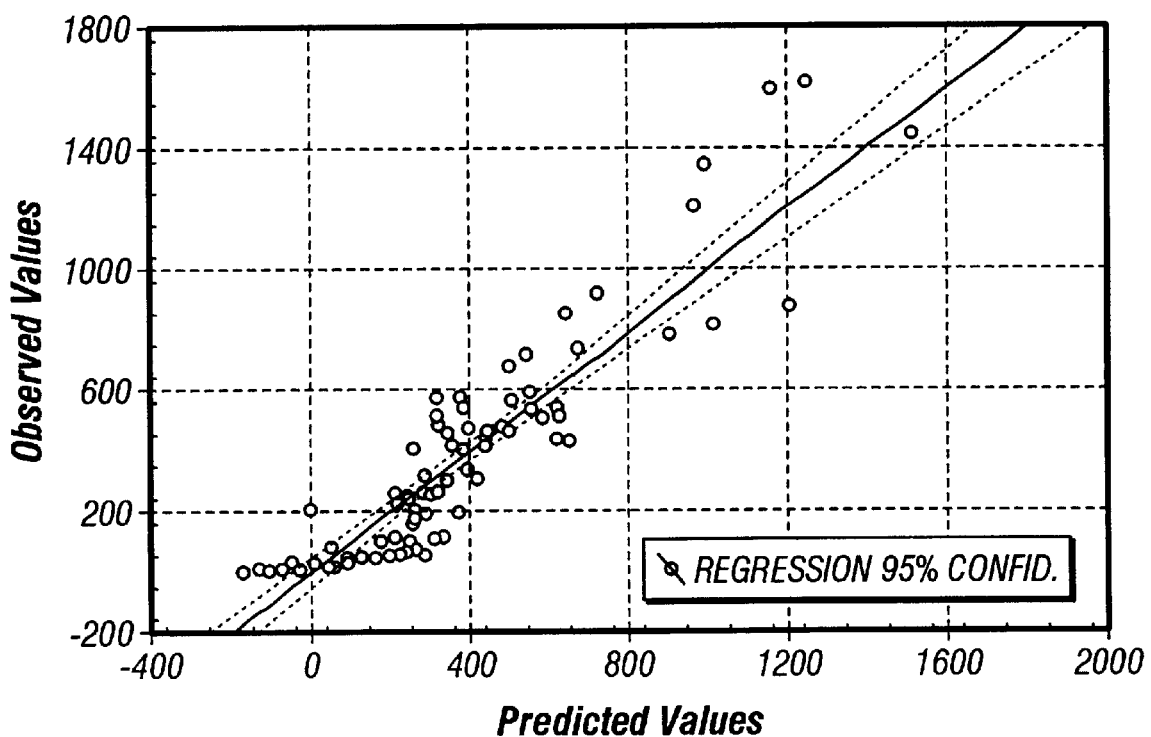
FIGS. 27 and 27A illustrate a regression for dependent variable T2 (geometric mean at 2.4 ms echo spacing) in terms of API gravity, reciprocal viscosity and fluorescence emission at wavelengths 395 and 405 nanometers during 360 nm ultraviolent excitation.
Figures 28, 28A:
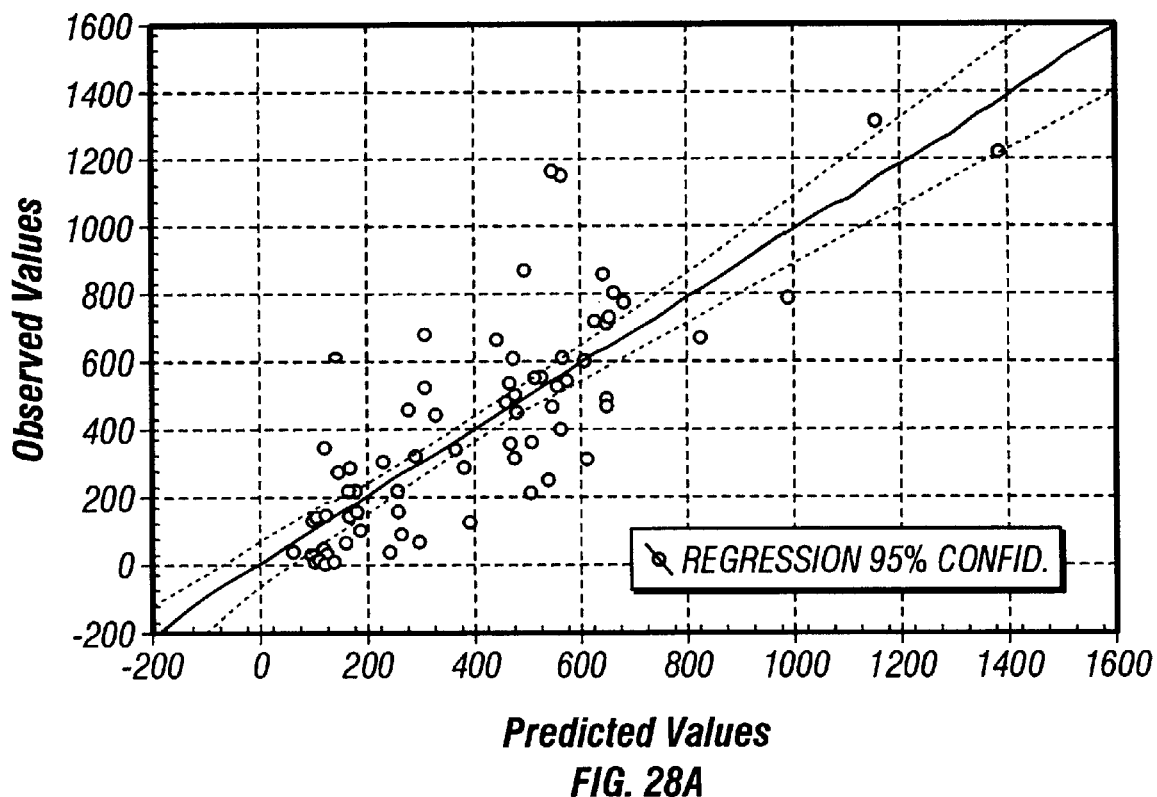
FIGS. 28 and 28A illustrate a regression for dependent variable T1 (geometric mean) in terms of transmittance channel 13 of the 17 channel NIR spectrometer fluorescence emission at wavelengths 395, 475, 535, 390 and 645 nanometers during 360 nm ultraviolent excitation.
Figures 29, 29A:
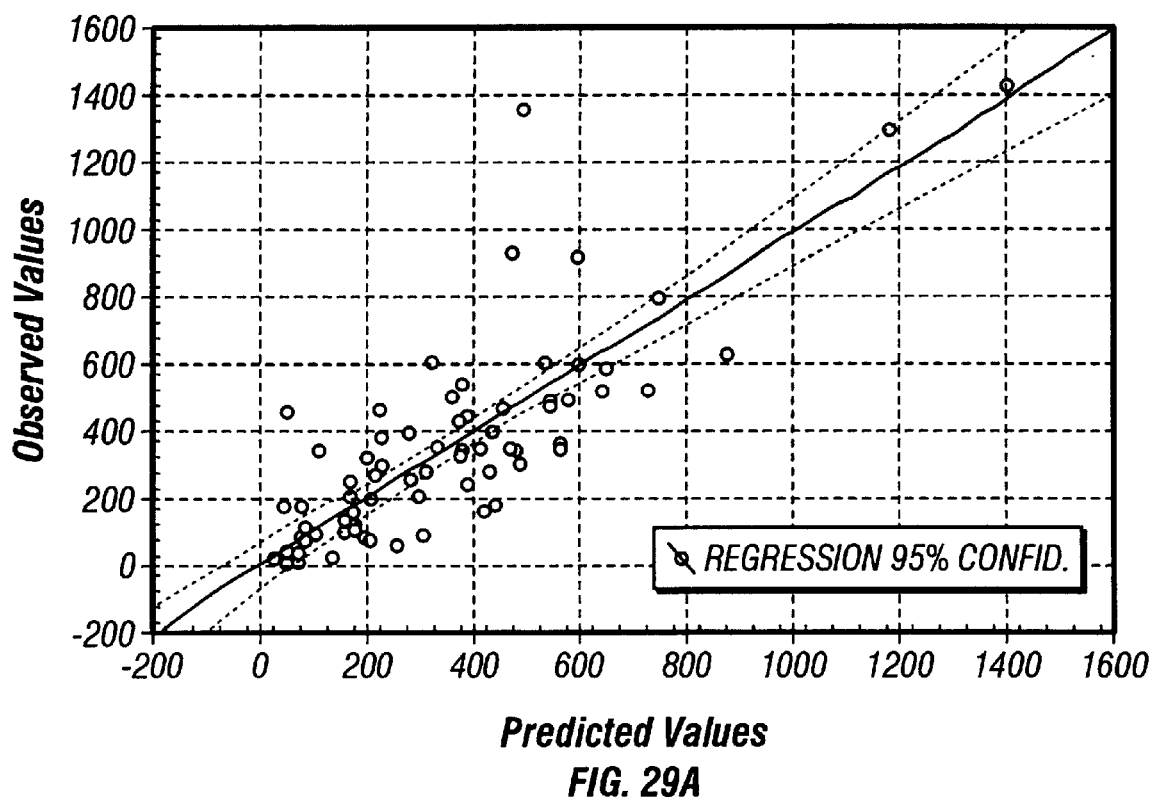
FIGS. 29 and 29A illustrate a regression for dependent variable T2 (geometric mean at 0.6 ms echo spacing) in terms of transmittance channel 13 of the 17 channel NIR spectrometer fluorescence emission at wavelengths 405, 440, 420, 535 and 460 nanometers during 360 nm ultraviolent excitation.

FIGS. 26 and 26A illustrate a regression for dependent variable T1 (geometric mean at 0.6 ms echo spacing) in terms of API gravity, reciprocal viscosity and fluorescence emission at wavelengths 395 and 405 nanometers during 360 nm ultraviolent excitation. FIGS. 27 and 27A illustrate a regression for dependent variable T2 (geometric mean at 2.4 ms echo spacing) in terms of API gravity, reciprocal viscosity and fluorescence emission at wavelengths 395 and 405 nanometers during 360 nm ultraviolent excitation. FIGS. 28 and 28A illustrate a regression for dependent variable T1 (geometric mean) in terms of transmittance channel 13 of the 17 channel NIR spectrometer fluorescence emission at wavelengths 395, 475, 535, 390 and 645 nanometers during 360 nm ultraviolent excitation. FIGS. 29 and 29A illustrate a regression for dependent variable T2 (geometric mean at 0.6 ms echo spacing) in terms of transmittance channel 13 of the 17 channel NIR spectrometer fluorescence emission at wavelengths 405, 440, 420, 535 and 460 nanometers during 360 nm ultraviolent excitation.

Figures 30, 30A:
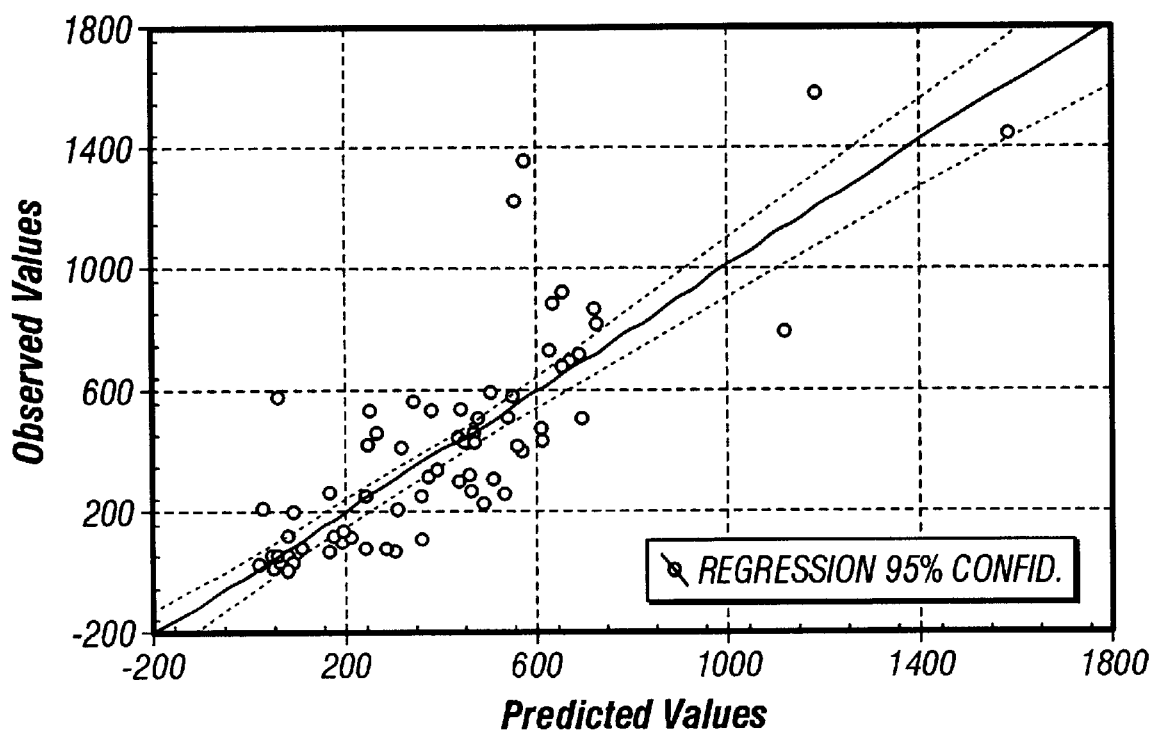
FIGS. 30 and 30A illustrate a regression for dependent variable T2 (geometric mean at 2.4 ms echo spacing) in terms of transmittance channel 13 of the 17 channel NIR spectrometer fluorescence emission at wavelengths 395, 405, 415, and 440 nanometers during 360 nm ultaviolent excitation.
Figures 31, 31A:
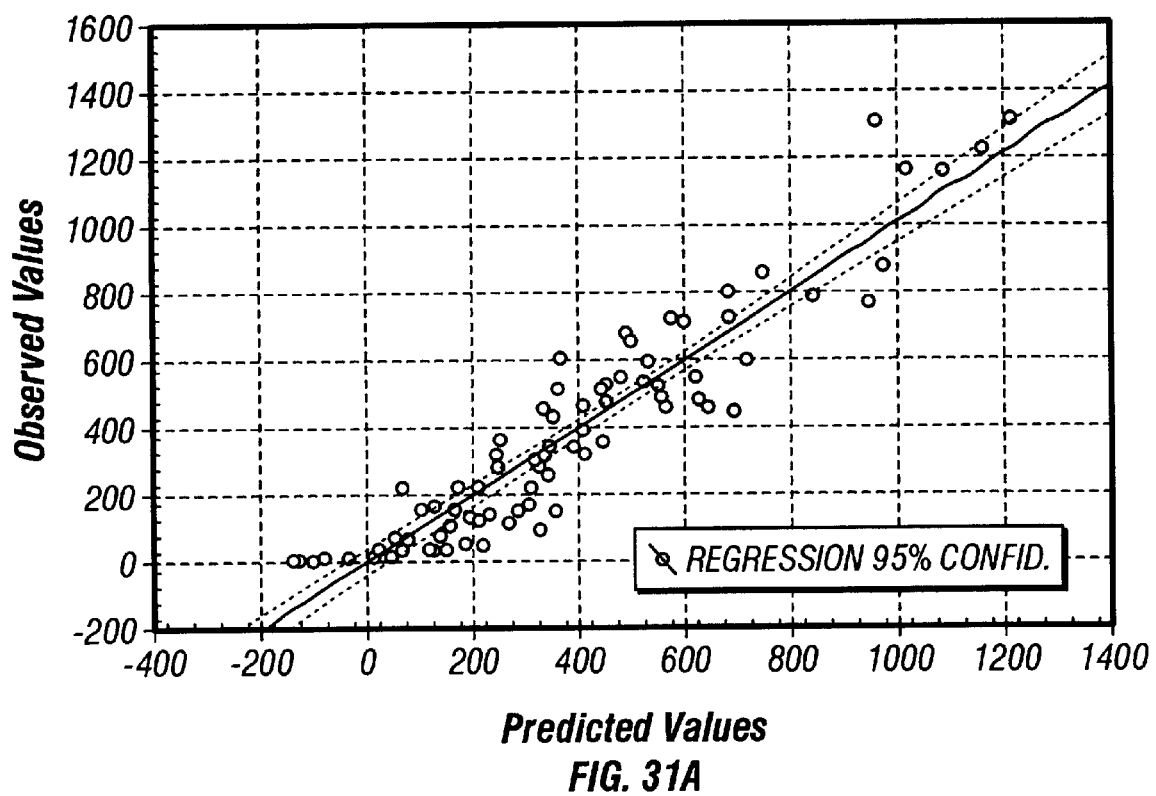
FIGS. 31 and 31A illustrate a regression for dependent variable T1 (geometric mean) in terms of API gravity, reciprocal viscosity (RCPOISE) and transmittance at channels 14, 15 and 17.
Figures 32, 32A:
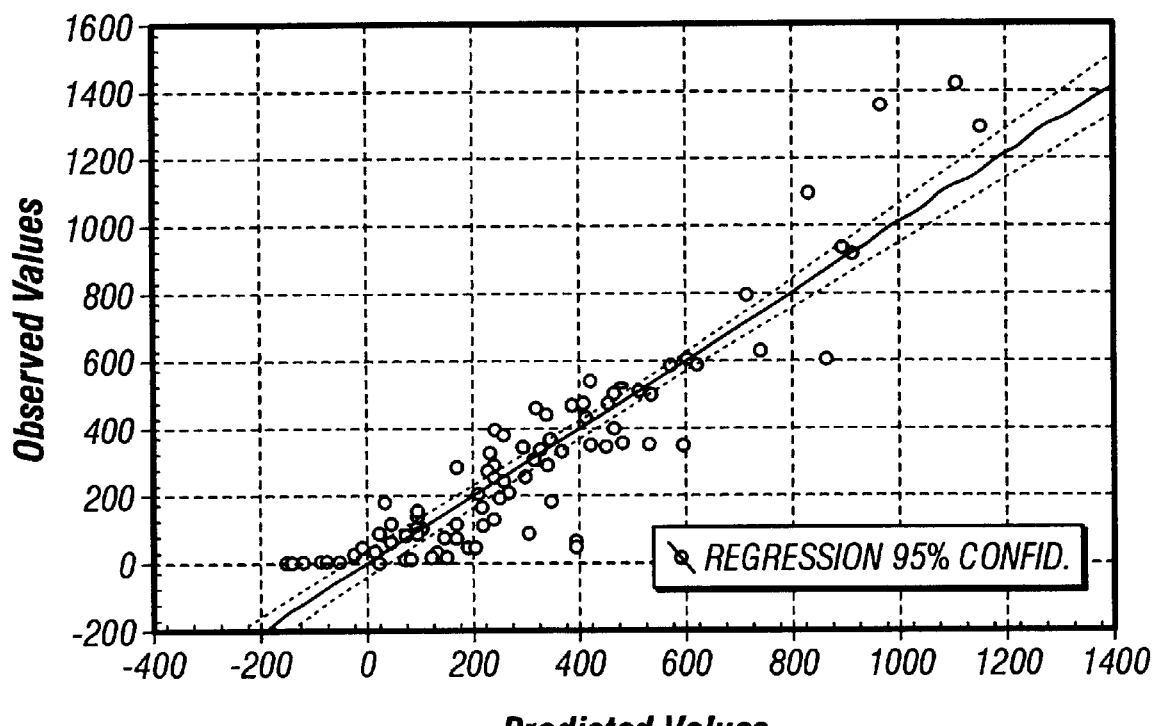
FIGS. 32 and 32A illustrate a regression for dependent variable T2 (geometric mean at 0.6 ms echo spacing) in terms of API gravity, reciprocal viscosity (RCPOISE) and transmittance at channels 13, 15 and 16 and absorbance at channels 10 and 12.
Figures 33, 33A:
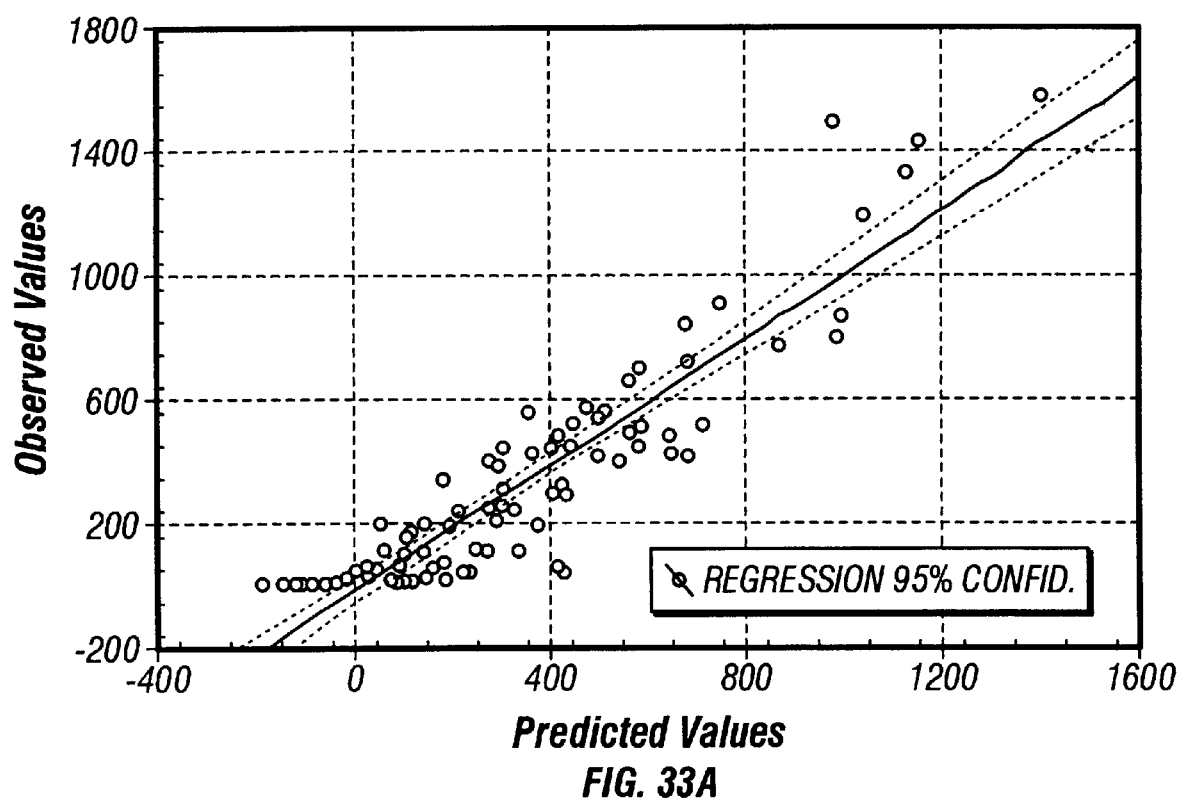
FIGS. 33 and 33A illustrate a regression for dependent variable T2 (geometric mean at 2.4 ms echo spacing) in terms of API gravity, reciprocal viscosity (RCPOISE) and transmittance at channels 13, 15 and 16.

FIGS. 30 and 30A illustrate a regression for dependent variable T2 (geometric mean at 2.4 ms echo spacing) in terms of transmittance channel 13 of the 17 channel NIR spectrometer fluorescence emission at wavelengths 395, 405, 415, and 440 nanometers during 360 nm ultaviolent excitation. FIGS. 31 and 31A illustrate a regression for dependent variable T1 (geometric mean) in terms of API gravity, reciprocal viscosity (RCPOISE) and transmittance at channels 14, 15 and 17. FIGS. 32 and 32A illustrate a regression for dependent variable T2 (geometric mean at 0.6 ms echo spacing) in terms of API gravity, reciprocal viscosity (RCPOISE) and transmittance at channels 13, 15 and 16 and absorbance at channels 10 and 12; and FIGS. 33 and 33A illustrate a regression for dependent variable T2 (geometric mean at 2.4 ms echo spacing) in terms of API gravity, reciprocal viscosity (RCPOISE) and transmittance at channels 13, 15 and 16.

The foregoing description have been give by way of example only and is not intended to limit the scope of the claims which are defined by the following claims.

What is claimed is:

1. A method for predicting NMR values T1, T2 from NIR spectra for a down hole hydrocarbon sample comprising the steps for:

(a) measuring NMR decay time values T1, T2 for a plurality of known hydrocarbon samples;

(b) measuring NIR absorbance spectra for the plurality of known hydrocarbon samples;

(c) generating a correlation between the NMR decay time values T1, T2 and the absorbance spectra for the known hydrocarbon samples;

(d) measuring the NIR spectra for an unknown hydrocarbon sample taken down hole; and (e) predicting the NMR decay time values T1, T2 for the unknown hydrocarbon sample using the correlation between the NMR decay time values T1, T2 and NIR spectra.

2. The method of claim 1 wherein the absorbance spectra is measured for 17 channels of infrared spectra.

3. The method of claim 2 wherein the 17 channels of infrared spectra comprise center wavelengths at 425.0, 475.0, 525.0, 575.0, 631.5, 694.0, 756.5, 819.0, 881.5, 944.0, 1006.5, 1069.0, 1300.0, 1420.0 1600.0 1740.0 and 1935.0 nanometers.

4. The method of claim 1 wherein step (c) comprises generating a correlation between the NMR decay times T1, T2 and selected transforms of the spectra for the known hydrocarbon samples.

5. An apparatus for predicting NMR values T1, T2 from NIR spectra for a down hole hydrocarbon sample comprising:

(a) a laboratory instrument for measuring NMR decay time values T1, T2 for a plurality of known hydrocarbon samples;

(b) a laboratory instrument for measuring NIR absorbance spectra for the plurality of known hydrocarbon samples;

(c) a computer programmed to generate a correlation between the NMR decay time values T1, T2 and the absorbance spectra for the known hydrocarbon samples;

(d) a down hole infrared spectrometer for measuring and storing the NIR spectra for an unknown hydrocarbon sample taken down hole; and (e) the computer further programmed for predicting the NMR decay time values T1, T2 for the unknown hydrocarbon sample using the correlation between the NMR decay time values T1, T2 and NIR spectra.

6. The apparatus of claim 5 wherein the absorbance spectra are measured for 17 channels of infrared spectra.

7. The apparatus of claim 6 wherein the 17 channels of infrared spectra comprise center wavelengths at 425.0, 475.0, 525.0, 575.0, 631.5, 694.0, 756.5, 819.0, 881.5, 944.0, 1006.5, 1069.0, 1300.0, 1420.0, 1600.0 1740.0 and 1935.0 nanometers.

8. The method of claim 5 wherein element (c) comprises a computer programmed to generate a correlation between the NMR decay time values T1, T2 and selected transforms of the spectra for the known hydrocarbon samples.

* * * * *